US010881684B2

(12) United States Patent
Kaminski et al.

(10) Patent No.: US 10,881,684 B2
(45) Date of Patent: Jan. 5, 2021

(54) ARTIFICIAL INVAPLEX FORMULATED WITH DEACYLATED LIPOPOLYSACCHARIDE

(71) Applicant: THE UNITED STATES OF AMERICA, as represented by THE SECRETARY OF THE ARMY, ON BEHALF OF THE WALTER REED ARMY INSTITUTE OF RESEARCH, Fort Detrick, MD (US)

(72) Inventors: Robert W. Kaminski, Germantown, MD (US); Kevin R. Turbyfill, Odenton, MD (US); Edwin V. Oaks, Gambrills, MD (US); Kristen Clarkson, Silver Spring, MD (US)

(73) Assignee: The United States Government as represented by the Secretary of the Army, Fort Detrick, MD (US)

( * ) Notice: Subject to any disclaimer, the term of this patent is extended or adjusted under 35 U.S.C. 154(b) by 51 days.

(21) Appl. No.: 16/083,497

(22) PCT Filed: Jun. 26, 2017

(86) PCT No.: PCT/US2017/039200
§ 371 (c)(1),
(2) Date: Sep. 8, 2018

(87) PCT Pub. No.: WO2018/005324
PCT Pub. Date: Jan. 4, 2018

(65) Prior Publication Data

US 2019/0099442 A1 Apr. 4, 2019

Related U.S. Application Data

(60) Provisional application No. 62/354,907, filed on Jun. 27, 2016.

(51) Int. Cl.
*A61K 31/739* (2006.01)
*A61K 39/39* (2006.01)
(Continued)

(52) U.S. Cl.
CPC .......... *A61K 31/739* (2013.01); *A61K 9/0019* (2013.01); *A61K 38/16* (2013.01);
(Continued)

(58) Field of Classification Search
CPC ............ A61K 39/0283; A61K 47/6921; A61K 2039/70; A61K 9/0019;
(Continued)

(56) References Cited

U.S. PATENT DOCUMENTS

2013/0149329 A1* 6/2013 Picking .............. A61K 39/0283 424/192.1
2016/0120967 A1 5/2016 Aparin et al.

FOREIGN PATENT DOCUMENTS

WO WO-2014196887 A1 * 12/2014 ......... A61K 39/0258

OTHER PUBLICATIONS

Ranallo et al., (Infect and Imm. Jan. 2010. vol. 78; No. 1; pp. 400-412). (Year: 2010).*
(Continued)

*Primary Examiner* — Jana A Hines
(74) *Attorney, Agent, or Firm* — Leigh Callander

(57) ABSTRACT

Disclosed herein are artificial Invaplexes comprising deacylated lipopolysaccharides and methods of making and using thereof.

18 Claims, 30 Drawing Sheets

(51) Int. Cl.

| | |
|---|---|
| ***A61P 37/04*** | (2006.01) |
| ***A61K 39/112*** | (2006.01) |
| ***C07K 14/25*** | (2006.01) |
| ***A61K 38/16*** | (2006.01) |
| ***A61K 45/06*** | (2006.01) |
| ***A61K 47/69*** | (2017.01) |
| ***A61K 47/61*** | (2017.01) |
| ***A61K 9/00*** | (2006.01) |
| ***A61K 39/00*** | (2006.01) |

(52) U.S. Cl.

CPC ........ *A61K 38/164* (2013.01); *A61K 39/0283* (2013.01); *A61K 39/39* (2013.01); *A61K 45/06* (2013.01); *A61K 47/61* (2017.08); *A61K 47/6921* (2017.08); *A61P 37/04* (2018.01); *C07K 14/25* (2013.01); *A61K 2039/543* (2013.01); *A61K 2039/55572* (2013.01); *A61K 2039/70* (2013.01)

(58) Field of Classification Search

CPC ........ A61K 2039/55572; A61K 38/164; A61K 45/062; A61K 31/739; A61K 2039/543; A61K 47/61; A61K 38/16; A61K 39/39; A61K 2300/00; A61P 37/04; C07K 14/25

See application file for complete search history.

(56) References Cited

OTHER PUBLICATIONS

International Search Report received in PCT/US2017/039200 dated Sep. 29, 2017.

Written Opinion received in PCT/US2017/039200 dated Sep. 29, 2017.

Ranallo, et al., "Virulence, Inflammatory Potential, and Adaptive Immunity Induced by Shigella flexneri msbB Mutants", Jan. 1, 2010, Publisher: Infection and Immunity.

* cited by examiner

| Treatment (dose) | | Erythema | | | | | | | | Edema | | | | | | | |
|---|---|---|---|---|---|---|---|---|---|---|---|---|---|---|---|---|---|
| | | Administration Site 1 | | | | Administration Site 2 | | | | Administration Site 1 | | | | Administration Site 2 | | | |
| | | D0 | D1 | D2 | D3 | D21 | D22 | D23 | D24 | D0 | D1 | D2 | D3 | D21 | D22 | D23 | D24 |
| Invaplex$_{AR-WT}$ (WT-LPS; 0.25 μg) | AVG | 0 | --- | 0 | 0 | 0 | 0 | 0 | 0 | 0 | --- | 0 | 0 | 0 | 0 | 0 | 0 |
| | STDEV | 0 | --- | 0 | 0 | 0 | 0 | 0 | 0 | 0 | --- | 0 | 0 | 0 | 0 | 0 | 0 |
| Invaplex$_{AR-WT}$ (WT-LPS; 2.5 μg) | AVG | 0 | --- | 0 | 0 | 0 | 0 | 0 | 0 | 0 | --- | 0 | 0 | 0 | 0 | 0 | 0 |
| | STDEV | 0 | --- | 0 | 0 | 0 | 0 | 0 | 0 | 0 | --- | 0 | 0 | 0 | 0 | 0 | 0 |
| Invaplex$_{AR-WT}$ (WT-LPS; 25 μg) | AVG | 0 | --- | 0.2 | 0.2 | 0 | 0 | 0.5 | 0 | 0 | --- | 3 | 1.8 | 0 | 0.2 | 2.2 | 2.4 |
| | STDEV | 0 | --- | 0.4 | 0.4 | 0 | 0 | 0.6 | 0 | 0 | --- | 0 | 0.4 | 0 | 0.4 | 1.3 | 1.3 |
| Invaplex$_{AR-Detox}$ (Δ*msb*B1 LPS; 0.25 μg) | AVG | 0 | --- | 0 | 0 | 0 | 0 | 0 | 0 | 0 | --- | 0 | 0 | 0 | 0 | 0 | 0.6 |
| | STDEV | 0 | --- | 0 | 0 | 0 | 0 | 0 | 0 | 0 | --- | 0 | 0 | 0 | 0 | 0 | 1.3 |
| Invaplex$_{AR-Detox}$ (Δ*msb*B1 LPS; 2.5 μg) | AVG | 0 | --- | 0.2 | 1 | 0 | 0.2 | 0 | 0 | 0 | --- | 0.6 | 1 | 0 | 0 | 0 | 0 |
| | STDEV | 0 | --- | 0.4 | 1.2 | 0 | 0.4 | 0 | 0 | 0 | --- | 0.5 | 0 | 0 | 0 | 0 | 0 |
| Invaplex$_{AR-Detox}$ (Δ*msb*B1 LPS; 25 μg) | AVG | 0 | --- | 0 | 0.2 | 0 | 2 | 2 | 0 | 0 | --- | 1.8 | 0.8 | 0 | 2.8 | 3 | 0.2 |
| | STDEV | 0 | --- | 0 | 0.4 | 0 | 0 | 0 | 0 | 0 | --- | 1.1 | 0.4 | 0 | 0.4 | 0 | 0.4 |
| Invaplex$_{AR-Detox}$ (Δ*msb*B2 LPS; 0.25 μg) | AVG | 0 | --- | 0 | 0 | 0 | 0 | 0 | 0 | 0 | --- | 0 | 0.2 | 0 | 0 | 0 | 0 |
| | STDEV | 0 | --- | 0 | 0 | 0 | 0 | 0 | 0 | 0 | --- | 0 | 0.4 | 0 | 0 | 0 | 0 |
| Invaplex$_{AR-Detox}$ (Δ*msb*B2 LPS; 2.5 μg) | AVG | 0 | --- | 0 | 0 | 0 | 0 | 0 | 0 | 0 | --- | 0 | 0 | 0 | 0 | 0 | 0 |
| | STDEV | 0 | --- | 0 | 0 | 0 | 0 | 0 | 0 | 0 | --- | 0 | 0 | 0 | 0 | 0 | 0 |
| Invaplex$_{AR-Detox}$ (Δ*msb*B2 LPS; 25 μg) | AVG | 0 | --- | 0.4 | 0.2 | 0 | 0.7 | 0.3 | 0 | 0 | --- | 3 | 2.6 | 0 | 2.5 | 3 | 0 |
| | STDEV | 0 | --- | 0.5 | 0.4 | 0 | 0.6 | 0.5 | 0 | 0 | --- | 0 | 0.5 | 0 | 0.6 | 0 | 0 |
| Invaplex$_{AR-Detox}$ (Δ*msb*B1/2 LPS; 0.25 μg) | AVG | 0 | --- | 0 | 0 | 0 | 0 | 0 | 0 | 0 | --- | 0 | 0 | 0 | 0 | 0 | 0 |
| | STDEV | 0 | --- | 0 | 0 | 0 | 0 | 0 | 0 | 0 | --- | 0 | 0 | 0 | 0 | 0 | 0 |
| Invaplex$_{AR-Detox}$ (Δ*msb*B1/2 LPS; 2.5 μg) | AVG | 0 | --- | 0 | 0 | 0 | 0 | 0 | 0 | 0 | --- | 0 | 0 | 0 | 0 | 0 | 0 |
| | STDEV | 0 | --- | 0 | 0 | 0 | 0 | 0 | 0 | 0 | --- | 0 | 0 | 0 | 0 | 0 | 0 |
| Invaplex$_{AR-Detox}$ (Δ*msb*B1/2 LPS; 25 μg) | AVG | 0 | --- | 1 | 1 | 0 | 0 | 0 | 0 | 0 | --- | 2.8 | 2 | 0 | 0 | 0 | 2 |
| | STDEV | 0 | --- | 0 | 0.7 | 0 | 0 | 0 | 0 | 0 | --- | 0.4 | 0.7 | 0 | 0 | 0 | 1.2 |
| 0.9% saline | AVG | 0 | --- | 0 | 0 | 0 | 0 | 0 | 0 | 0 | --- | 0 | 0 | 0 | 0 | 0 | 0 |
| | STDEV | 0 | --- | 0 | 0 | 0 | 0 | 0 | 0 | 0 | --- | 0 | 0 | 0 | 0 | 0 | 0 |

Edema and erythema scores > 0 are highlighted in light gray, medium gray, and black (having white text) corresponding to mean scores of < 1, 1-2, or >2, respectively.

Figure 12

Summary of Administration Site Observations:
Induration observed at administration site 1 and 2

| Grp | Treatment (dose) | | Induration (mm$^2$) | | | | | | | |
|---|---|---|---|---|---|---|---|---|---|---|
| | | | Administration Site 1 | | | | Administration Site 2 | | | |
| | | | D0 | D1 | D2 | D3 | D21 | D22 | D23 | D24 |
| 1 | Invaplex$_{AR-WT}$ (WT-LPS; 0.25 μg) | AVG | 0 | --- | 0 | 0 | 0 | 0 | 0 | 0 |
| | | STDEV | 0 | --- | 0 | 0 | 0 | 0 | 0 | 0 |
| 2 | Invaplex$_{AR-WT}$ (WT-LPS; 2.5 μg) | AVG | 0 | --- | 0 | 0 | 0 | U | 0 | 0 |
| | | STDEV | 0 | --- | 0 | 0 | 0 | --- | 0 | 0 |
| 3 | Invaplex$_{AR-WT}$ (WT-LPS; 25 μg) | AVG | 0 | --- | U | U | 0 | U | U | U |
| | | STDEV | 0 | --- | --- | --- | 0 | --- | --- | --- |
| 7 | Invaplex$_{AR-Detox}$ (Δ*msb*B1 LPS; 0.25 μg) | AVG | 0 | --- | 0 | 0 | 0 | U | U | U |
| | | STDEV | 0 | --- | 0 | 0 | 0 | --- | --- | --- |
| 8 | Invaplex$_{AR-Detox}$ (Δ*msb*B1 LPS; 2.5 μg) | AVG | 0 | --- | 0 | U | 0 | U | 0 | 0 |
| | | STDEV | 0 | --- | 0 | --- | 0 | --- | 0 | 0 |
| 9 | Invaplex$_{AR-Detox}$ (Δ*msb*B1 LPS; 25 μg) | AVG | 0 | --- | 0 | U | 0 | U | U | 0 |
| | | STDEV | 0 | --- | 0 | --- | 0 | --- | --- | 0 |
| 13 | Invaplex$_{AR-Detox}$ (Δ*msb*B2 LPS; 0.25 μg) | AVG | 0 | --- | 0 | 0 | 0 | U | 0 | 0 |
| | | STDEV | 0 | --- | 0 | 0 | 0 | --- | 0 | 0 |
| 14 | Invaplex$_{AR-Detox}$ (Δ*msb*B2 LPS; 2.5 μg) | AVG | 0 | --- | 0 | 0 | 0 | U | 0 | 0 |
| | | STDEV | 0 | --- | 0 | 0 | 0 | --- | 0 | 0 |
| 15 | Invaplex$_{AR-Detox}$ (Δ*msb*B2 LPS; 25 μg) | AVG | 0 | --- | U | U | 0 | U | U | 0 |
| | | STDEV | 0 | --- | --- | --- | 0 | --- | --- | 0 |
| 19 | Invaplex$_{AR-Detox}$ (Δ*msb*B1/2 LPS; 0.25 μg) | AVG | 0 | --- | 0 | 0 | 0 | U | 0 | 0 |
| | | STDEV | 0 | --- | 0 | 0 | 0 | --- | 0 | 0 |
| 20 | Invaplex$_{AR-Detox}$ (Δ*msb*B1/2 LPS; 2.5 μg) | AVG | 0 | --- | 0 | 0 | 0 | U | 0 | 0 |
| | | STDEV | 0 | --- | 0 | 0 | 0 | --- | 0 | 0 |
| 21 | Invaplex$_{AR-Detox}$ (Δ*msb*B1/2 LPS; 25 μg) | AVG | 0 | --- | U | U | 0 | U | 0 | U |
| | | STDEV | 0 | --- | --- | --- | 0 | --- | 0 | --- |
| 25 | 0.9% Saline | AVG | 0 | --- | 0 | 0 | 0 | 0 | 0 | 0 |
| | | STDEV | 0 | --- | 0 | 0 | 0 | 0 | 0 | 0 |

Figure 13

*Shigella* antigen-specific serum IgA and IgG endpoint titers on day 35 from mice intradermally immunized with $Invaplex_{AR-WT}$ or $Invaplex_{AR-Detox}$

| Grp | Treatment | Anti-*S. flexneri* 2a LPS | Anti-*S. flexneri* 2a Invaplex 24 | Anti-IpaB | | Anti-IpaC | |
|---|---|---|---|---|---|---|---|
| | | IgA | IgA | IgA | IgG | IgA | IgG |
| 1 | $Invaplex_{AR-WT}$ (WT-LPS; 0.25 µg) | 45 ± 0* (0%) | 45 ± 0 (0%) | 90 ± 68 (40%) | 15201 ± 8146 (100%) | 59 ± 25 (0%) | 1091 ± 2341 (100%) |
| 7 | $Invaplex_{AR-Detox}$ (Δ*msb*B1 LPS; 0.25 µg) | 45 ± 0 (0%) | 45 ± 0 (0%) | 59 ± 25 (0%) | 8731 ± 3864 (100%) | 59 ± 60 (20%) | 475 ± 4984 (40%) |
| 13 | $Invaplex_{AR-Detox}$ (Δ*msb*B2 LPS; 0.25 µg) | 78 ± 137 (20%) | 59 ± 60 (20%) | 45 ± 0 (0%) | 15201 ± 16087 (100%) | 45 ± 0 (0%) | 414 ± 523 (80%) |
| 19 | $Invaplex_{AR-Detox}$ (Δ*msb*B1/2 LPS; 0.25 µg) | 103 ± 74 (60%) | 59 ± 25 (0%) | 78 ± 55 (20%) | 30401 ± 16292 (100%) | 52 ± 20 (0%) | 238 ± 2526 (20%) |
| 2 | $Invaplex_{AR-WT}$ (WT-LPS; 2.5 µg) | 45 ± 0 (0%) | 59 ± 20 (0%) | 414 ± 1196 (80%) | 40115 ± 69132 (100%) | 360 ± 691 (80%) | 7600 ± 22413 (80%) |
| 8 | $Invaplex_{AR-Detox}$ (Δ*msb*B1 LPS; 2.5 µg) | 78 ± 55 (20%) | 59 ± 60 (20%) | 45 ± 0 [a] (0%) | 92160 ± 50478 (100%) | 103 ± 293 (20%) | 2880 ± 81716 (100%) |
| 14 | $Invaplex_{AR-Detox}$ (Δ*msb*B2 LPS; 2.5 µg) | 59 ± 25 (0%) | 78 ± 55 (20%) | 180 ± 764 (40%) | 139688 ± 299697 (100%) | 68 ± 141 [a] (20%) | 360 ± 10244 [a] (20%) |
| 20 | $Invaplex_{AR-Detox}$ (Δ*msb*B1/2 LPS; 2.5 µg) | 45 ± 0 (0%) | 45 ± 0 (0%) | 52 ± 20 [a] (0%) | 30401 ± 150135 (100%) | 59 ± 60 [a] (20%) | 1440 ± 20142 (80%) |
| 3 | $Invaplex_{AR-WT}$ (WT-LPS; 25 µg) | 59 ± 25 (0%) | 273 ± 314 (80%) | 3308 ± 1932 (100%) | 972688 ± 521442 (100%) | 3800 ± 1577 (100%) | 211728 ± 267899 (100%) |
| 9 | $Invaplex_{AR-Detox}$ (Δ*msb*B1 LPS; 25 µg) | 90 ± 133 (20%) | 546 ± 197 (100%) | 475 ± 630 [a] (80%) | 320920 ± 320745 (100%) | 1654 ± 2005 (80%) | 211728 ± 326201 (100%) |
| 15 | $Invaplex_{AR-Detox}$ (Δ*msb*B2 LPS; 25 µg) | 119 ± 130 (40%) | 313 ± 80 (100%) | 78 ± 74 [a] (40%) | 558754 ± 480648 (100%) | 720 ± 1098 [a] (100%) | 184320 ± 0 (100%) |
| 21 | $Invaplex_{AR-Detox}$ (Δ*msb*B1/2 LPS; 25 µg) | 52 ± 20 (20%) | 313 ± 559 (80%) | 180 ± 588 [a] (60%) | 486423 ± 514778 (100%) | 950 ± 2278 (100%) | 211728 ± 151434 (100%) |

*Geometeric mean titer ± SD (percent responder)

Responder defined as an animal with a ≥ 4-fold increase in titer over baseline

[a] Significantly different endpoint titers as compared to groups immunized with dose-matched $Invaplex_{AR-WT}$ (WT-LPS) groups (two-way ANOVA; $p < 0.05$)

Figure 20

*Shigella* antigen-specific lung wash IgG endpoint titers on day 35 from mice intradermally immunized with Invaplex$_{AR-WT}$ or Invaplex$_{AR-Detox}$

| Grp | Treatment | Anti-*S. flexneri* 2a Invaplex 24 | Anti-IpaB | Anti-IpaC |
|---|---|---|---|---|
| 1 | Invaplex$_{AR-WT}$ (WT-LPS; 0.25 µg) | 5 ± 0 (0%) | 15 ± 18 (60%) | 6 ± 2 (0%) |
| 7 | Invaplex$_{AR-Detox}$ (Δ*msb*B1 LPS; 0.25 µg) | 5 ± 0 (0%) | 8 ± 7 (25%) | 5 ± 0 (0%) |
| 13 | Invaplex$_{AR-Detox}$ (Δ*msb*B2 LPS; 0.25 µg) | 5 ± 0 (0%) | 20 ± 21 (50%) | 5 ± 0 (0%) |
| 19 | Invaplex$_{AR-Detox}$ (Δ*msb*B1/2 LPS; 0.25 µg) | 5 ± 0 (0%) | 25 ± 12 (100%) | 5 ± 0 (0%) |
| 2 | Invaplex$_{AR-WT}$ (WT-LPS; 2.5 µg) | 8 ± 7 (20%) | 30 ± 62 (80%) | 13 ± 14 (40%) |
| 8 | Invaplex$_{AR-Detox}$ (Δ*msb*B1 LPS; 2.5 µg) | 15 ± 31 (40%) | 35 ± 24 (100%) | 30 ± 133 (60%) |
| 14 | Invaplex$_{AR-Detox}$ (Δ*msb*B2 LPS; 2.5 µg) | 10 ± 8 (40%) | 61 ± 128 (80%) | 5 ± 0 (0%) |
| 20 | Invaplex$_{AR-Detox}$ (Δ*msb*B1/2 LPS; 2.5 µg) | 8 ± 3 (0%) | 28 ± 31 (75%) | 8 ± 18 (25%) |
| 3 | Invaplex$_{AR-WT}$ (WT-LPS; 25 µg) | 70 ± 121 (100%) | 485 ± 429 (100%) | 160 ± 244 (100%) |
| 9 | Invaplex$_{AR-Detox}$ (Δ*msb*B1 LPS; 25 µg) | 139 ± 100 (100%) | 243 ± 261 (100%) | 139 ± 248 (80%) |
| 15 | Invaplex$_{AR-Detox}$ (Δ*msb*B2 LPS; 25 µg) | 70 ± 268 (100%) | 320 ± 1058 (100%) | 211 ± 223 (100%) |
| 21 | Invaplex$_{AR-Detox}$ (Δ*msb*B1/2 LPS; 25 µg) | 80 ± 44 (100%) | 368 ± 453 (100%) | 184 ± 236 (100%) |

*Geometeric mean titer ± SD (percent responder)
Responder defined as an animal with a ≥ 4-fold increase in titer over baseline

Figure 22

Protective efficacy after intrarectal challenge of guinea pigs intranasally immunized with $Invaplex_{AR-WT}$ or $Invaplex_{AR-Detox}$

| Grp | Treatment (dose µg) | Protected [a] / Total | Protective Efficacy [b] | p value [c] |
|---|---|---|---|---|
| 1 | $Invaplex_{AR-WT}$ (WT-LPS; 25 µg) | 0/5 | 0% | 1.0 |
| **3** | **$Invaplex_{AR-WT}$ (WT-LPS; 100 µg)** | **3/5** | **60%** | **0.0275** |
| 5 | $Invaplex_{AR-Detox}$ (Δ*msb*B1/2 LPS; 25 µg) | 1/5 | 20% | 0.3571 |
| **7** | **$Invaplex_{AR-Detox}$ (Δ*msb*B1/2 LPS; 100 µg)** | **3/5** | **60%** | **0.0275** |
| 9 | Saline | 0/5 | 0% | --- |

Guinea pigs were intranasally immunized on day 0, 14, and 28 as indicated above. Animals were rectally challenged with $3.5 \times 10^{10}$ cfu of *S. flexneri* 2a, 2457T on day 56 (4 weeks after the last immunization).
[a] Protection defined as a composite disease score ≤ 8 at 48 hours post challenge.
[b] Protective efficacy calculated as [(percent protection treatment - percent protection control)/percent protection control].
[c] Fisher's exact test (compared to saline-immunized controls).
Bolded treatment groups were significantly protected from challenge as compared to control group.

Figure 23

*Shigella* LPS and Invaplex-specific serum IgA and IgG endpoint titers on day 42 from guinea pigs intranasally immunized with Invaplex$_{AR\text{-}WT}$ or Invaplex$_{AR\text{-}Detox}$

| Grp | Treatment | Anti-*S. flexneri* 2a LPS (% responder) | | Anti-*S. flexneri* 2a Invaplex 24 (% responder) | |
|---|---|---|---|---|---|
| | | IgG | IgA | IgG | IgA |
| 1 | Invaplex$_{AR\text{-}WT}$ (WT-LPS; 25 μg) | 180 ± 277[a] (40%)[b] | 45 ± 0 (0%) | 6617 ± 8146 (100%) | 1091 ± 966 (100%) |
| 5 | Invaplex$_{AR\text{-}Detox}$ (Δ*msb*B1/2 LPS; 25 μg) | 90 ± 0 (0%) | 45 ± 0 (0%) | 5014 ± 1288 (100%) | 360 ± 1183 (80%) |
| 3 | Invaplex$_{AR\text{-}WT}$ (WT-LPS; 100 μg) | 238 ± 549 (40%) | 52 ± 20 (0%) | 15201 ± 15456 (100%) | 475 ± 503 (100%) |
| 7 | Invaplex$_{AR\text{-}Detox}$ (Δ*msb*B1/2 LPS; 100 μg) | 207 ± 148 (60%) | 45 ± 0 (0%) | 11520 ± 8735 (100%) | 207 ± 121 (80%) |
| 9 | Saline | 90 ± 0 (0%) | 45 ± 0 (0%) | 90 ± 0 (0%) | 90 ± 49 (20%) |

a: Geometeric mean titer ± SD
b: Percent responder in group. Responder defined as an animal with a ≥ 4-fold increase in titer over baseline

Figure 24

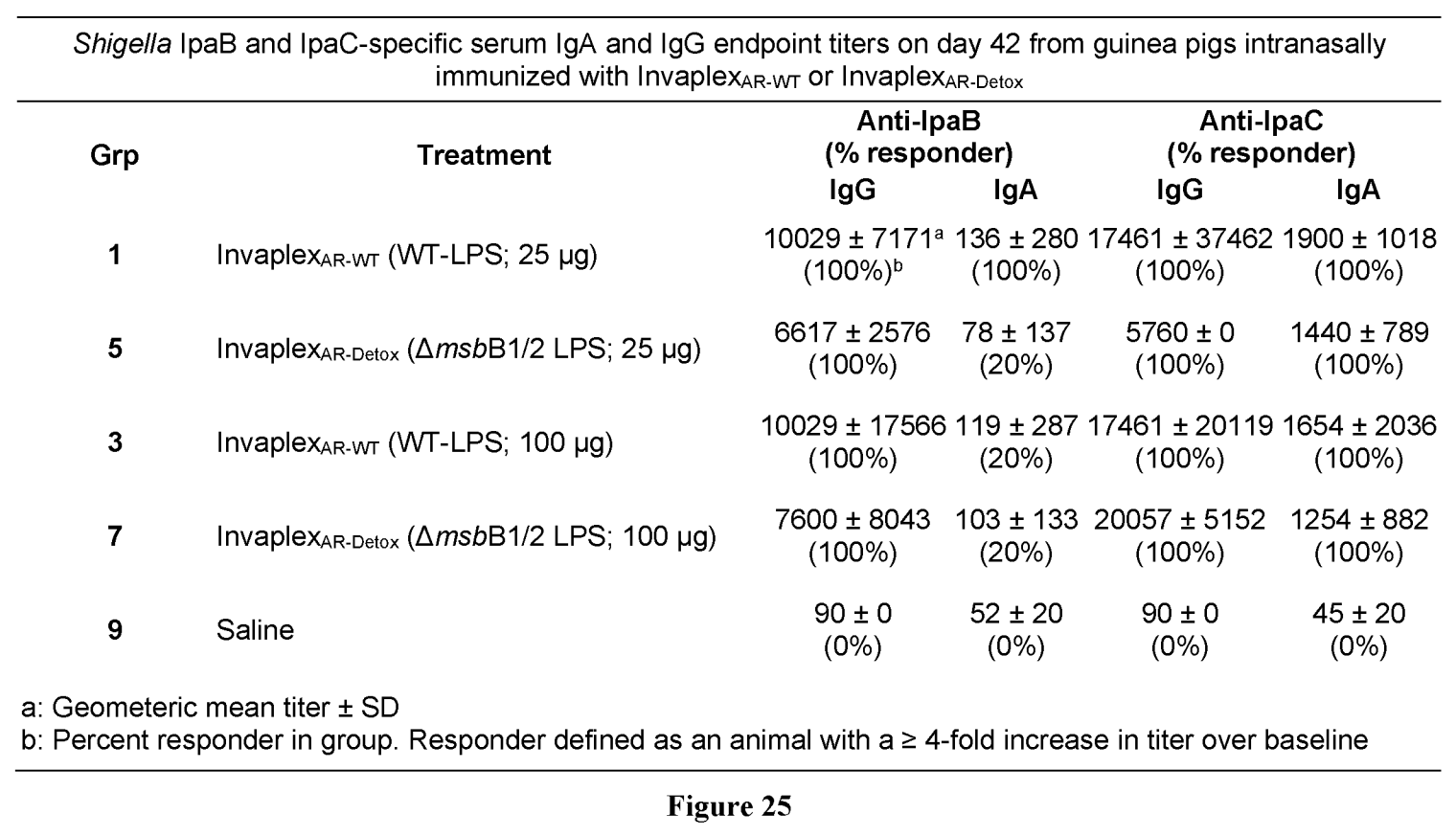

*Shigella* IpaB and IpaC-specific serum IgA and IgG endpoint titers on day 42 from guinea pigs intranasally immunized with $Invaplex_{AR\text{-}WT}$ or $Invaplex_{AR\text{-}Detox}$

| Grp | Treatment | Anti-IpaB (% responder) | | Anti-IpaC (% responder) | |
|---|---|---|---|---|---|
| | | IgG | IgA | IgG | IgA |
| 1 | $Invaplex_{AR\text{-}WT}$ (WT-LPS; 25 μg) | 10029 ± 7171[a] (100%)[b] | 136 ± 280 (100%) | 17461 ± 37462 (100%) | 1900 ± 1018 (100%) |
| 5 | $Invaplex_{AR\text{-}Detox}$ (Δ*msb*B1/2 LPS; 25 μg) | 6617 ± 2576 (100%) | 78 ± 137 (20%) | 5760 ± 0 (100%) | 1440 ± 789 (100%) |
| 3 | $Invaplex_{AR\text{-}WT}$ (WT-LPS; 100 μg) | 10029 ± 17566 (100%) | 119 ± 287 (20%) | 17461 ± 20119 (100%) | 1654 ± 2036 (100%) |
| 7 | $Invaplex_{AR\text{-}Detox}$ (Δ*msb*B1/2 LPS; 100 μg) | 7600 ± 8043 (100%) | 103 ± 133 (20%) | 20057 ± 5152 (100%) | 1254 ± 882 (100%) |
| 9 | Saline | 90 ± 0 (0%) | 52 ± 20 (0%) | 90 ± 0 (0%) | 45 ± 20 (0%) |

a: Geometeric mean titer ± SD
b: Percent responder in group. Responder defined as an animal with a ≥ 4-fold increase in titer over baseline

Figure 25

*Shigella* antigen-specific ocular IgA endpoint titers on day 42 from guinea pigs intranasally immunized with $Invaplex_{AR\text{-}WT}$ or $Invaplex_{AR\text{-}Detox}$

| Grp | Treatment | Anti-*S. flexneri* 2a LPS (% responder) | Anti-*S. flexneri* 2a Invaplex 24 (% responder) | Anti-IpaB (% responder) | Anti-IpaC (% responder) |
|---|---|---|---|---|---|
| 1 | $Invaplex_{AR\text{-}WT}$ (WT-LPS; 25 μg) | 8 ± 7[a] (20%)[b] | 46 ± 18 (100%) | 104 ± 92 (100%) | 80 ± 117 (80%) |
| 5 | $Invaplex_{AR\text{-}Detox}$ (Δ*msb*B1/2 LPS; 25 μg) | 5 ± 0 (0%) | 80 ± 118 (100%) | 70 ± 77 (100%) | 279 ± 596 (80%) |
| 3 | $Invaplex_{AR\text{-}WT}$ (WT-LPS; 100 μg) | 11 ± 15 (40%) | 70 ± 50 (100%) | 121 ± 104 (100%) | 160 ± 245 (100%) |
| 7 | $Invaplex_{AR\text{-}Detox}$ (Δ*msb*B1/2 LPS; 100 μg) | 7 ± 7 (20%) | 106 ± 112 (100%) | 160 ± 526 (100%) | 320 ± 469 (100%) |
| 9 | Saline | 5 ± 0 (0%) | 5 ± 0 (0%) | 5 ± 0 (0%) | 6 ± 2 (0%) |

a: Geometeric mean titer ± SD
b: Percent responder in group. Responder defined as an animal with a ≥ 4-fold increase in titer over baseline

Figure 26

*Shigella* anitgen-specific fecal IgA endpoint titers on day 35 from guinea pigs intranasally immunized with $Invaplex_{AR\text{-}WT}$ or $Invaplex_{AR\text{-}Detox}$

| Grp | Treatment | Anti-*S. flexneri* 2a LPS | Anti-*S. flexneri* 2a Invaplex 24 |
|---|---|---|---|
| **1** | $Invaplex_{AR\text{-}WT}$ (WT-LPS; 25 µg) | 5 | 20 |
| **5** | $Invaplex_{AR\text{-}Detox}$ (Δ*msb*B1/2 LPS; 25 µg) | 5 | 5 |
| **3** | $Invaplex_{AR\text{-}WT}$ (WT-LPS; 100 µg) | 5 | 20 |
| **7** | $Invaplex_{AR\text{-}Detox}$ (Δ*msb*B1/2 LPS; 100 µg) | 5 | 10 |
| **9** | Saline | 5 | 5 |

a: Geometeric mean titer ± SD b: Percent responder in group. Responder defined as an animal with a ≥ 4-fold increase in titer over baseline Fecal samples were collected for the group rather than per individual animals.

Figure 27

| Grp | Treatment | Route of Immunization | No. Eyes Protected[a] | No. Eyes Not Protected | Percent Disease[b] | Protective Efficacy[c] | P value[d] |
|---|---|---|---|---|---|---|---|
| 1 | $IVP_{AR\text{-}Detox}$ (25 µg) | Intranasal | 9 | 3 | 25% | 75% | 0.0003 |
| 2 | $IVP_{AR\text{-}Detox}$ (25 µg) | Intramuscular | 10 | 2 | 17% | 83% | < 0.0001 |
| 3 | $IVP_{AR\text{-}Detox}$ (5 µg) | Intramuscular | 4 | 8 | 67% | 33% | 0.0932 |
| 4 | $IVP_{AR\text{-}Detox}$ (25 µg) | Intradermal | 9 | 3 | 25% | 75% | 0.0003 |
| 5 | $IVP_{AR\text{-}Detox}$ (5 µg) | Intradermal | 5 | 7 | 58% | 42% | 0.0373 |
| 6 | Saline | Intranasal | 0 | 12 | 100% | --- | --- |

[a] Results reported are from day 5 post challenge
[b] Percent disease calculated as number of diseased eyes per group/total number of eyes
[c] Protective efficacy calculated as [{% disease (controls) - % disease (vaccines)} / % disease (controls)] X 100
[d] Fishers exact test of experimental groups compared to saline control group

Figure 28

ARTIFICIAL INVAPLEX FORMULATED WITH DEACYLATED LIPOPOLYSACCHARIDE

ACKNOWLEDGEMENT OF GOVERNMENT SUPPORT

This invention was made by employees of the United States Army Medical Research and Materiel Command, which is an agency of the United States Government. The Government has certain rights in the invention.

BACKGROUND OF THE INVENTION

1. Field of the Invention

The present invention relates to an artificial Invaplex formulated with deacylated lipopolysaccharide (LPS).

2. Description of the Related Art

Prior art artificial Invaplexes comprise wild-type lipopolysaccharide (WT-LPS) purified from gram-negative bacteria. When a prior art artificial Invaplex is injected into humans by either the sub-cutaneous, intramuscular, or intradermal route the risk of reactogenicity is high and may result in soreness, inflammation, and adverse systemic responses.

Therefore, a need exists for an artificial Invaplex that has a reduced risk of reactogenicity.

SUMMARY OF THE INVENTION

In some embodiments, the present invention provides an artificial Invaplex comprising one or more invasin proteins complexed with a deacylated lipopolysaccharide from a gram-negative bacterial strain. In some embodiments, the one or more invasin proteins are of a *Shigella* spp. In some embodiments, the deacylated lipopolysaccharide lacks one or more fatty acid chains as compared to the corresponding wild-type lipopolysaccharide. In some embodiments, the deacylated lipopolysaccharide lacks one fatty acid chain as compared to the corresponding wild-type lipopolysaccharide. In some embodiments, the deacylated lipopolysaccharide lacks two fatty acid chains as compared to the corresponding wild-type lipopolysaccharide. In some embodiments, the deacylated lipopolysaccharide lacks more than two fatty acid chains as compared to the corresponding wild-type lipopolysaccharide. In some embodiments, the gram-negative bacterial strain is a strain of *Shigella* spp. In some embodiments, the *Shigella* spp. is *S. boydii, S. dysenteriae, S. flexneri*, or *S. sonnei*. In some embodiments, the *Shigella* spp. is *S. flexneri*. In some embodiments, the gram-negative bacterial strain is a *Shigella* strain. In some embodiments, the gram-negative bacterial strain is an msbB mutant strain, such as a ΔmsbB1 mutant strain, a ΔmsbB2 mutant strain, or a ΔmsbB1/ΔmsbB2 mutant strain. In some embodiments, the gram-negative bacterial strain is a strain of a *Shigella* spp. that is an msbB mutant, such as a ΔmsbB1 mutant, a ΔmsbB2 mutant, or a ΔmsbB1/ΔmsbB2 mutant. In some embodiments, the gram-negative bacterial strain is WR10, WR20, or WR30. In some embodiments, the one or more invasin proteins are IpaB and IpaC, preferably from a *Shigella* spp. In some embodiments, the deacylated lipopolysaccharide was deacylated by enzymatic treatment. In some embodiments, the deacylated lipopolysaccharide was obtained from a strain of a *Shigella* spp. that lacks one or more genes responsible for lipopolysaccharide acylation. In some embodiments, the deacylated lipopolysaccharide was obtained from a strain of a *Shigella* spp. that has a loss-of-function mutation in one or more genes responsible for lipopolysaccharide acylation.

In some embodiments, the present invention provides a composition comprising the artificial Invaplex comprising one or more invasin proteins complexed with a deacylated lipopolysaccharide from a gram-negative bacterial strain and a pharmaceutically acceptable carrier. In some embodiments, the one or more invasin proteins are of a *Shigella* spp. In some embodiments, the deacylated lipopolysaccharide lacks one or more fatty acid chains as compared to the corresponding wild-type lipopolysaccharide. In some embodiments, the deacylated lipopolysaccharide lacks one fatty acid chain as compared to the corresponding wild-type lipopolysaccharide. In some embodiments, the deacylated lipopolysaccharide lacks two fatty acid chains as compared to the corresponding wild-type lipopolysaccharide. In some embodiments, the deacylated lipopolysaccharide lacks more than two fatty acid chains as compared to the corresponding wild-type lipopolysaccharide. In some embodiments, the gram-negative bacterial strain is a strain of *Shigella* spp. In some embodiments, the *Shigella* spp. is *S. boydii, S. dysenteriae, S. flexneri*, or *S. sonnei*. In some embodiments, the *Shigella* spp. is *S. flexneri*. In some embodiments, the gram-negative bacterial strain is a *Shigella* strain. In some embodiments, the gram-negative bacterial strain is an msbB mutant strain, such as a ΔmsbB1 mutant strain, a ΔmsbB2 mutant strain, or a ΔmsbB1/ΔmsbB2 mutant strain. In some embodiments, the gram-negative bacterial strain is a strain of a *Shigella* spp. that is an msbB mutant, such as a ΔmsbB1 mutant, a ΔmsbB2 mutant, or a ΔmsbB1/ΔmsbB2 mutant. In some embodiments, the gram-negative bacterial strain is WR10, WR20, or WR30. In some embodiments, the one or more invasin proteins are IpaB and IpaC, preferably from a *Shigella* spp. In some embodiments, the deacylated lipopolysaccharide was deacylated by enzymatic treatment. In some embodiments, the deacylated lipopolysaccharide was obtained from a strain of a *Shigella* spp. that lacks one or more genes responsible for lipopolysaccharide acylation. In some embodiments, the deacylated lipopolysaccharide was obtained from a strain of a *Shigella* spp. that has a loss-of-function mutation in one or more genes responsible for lipopolysaccharide acylation. In some embodiments, the composition further comprises an immunogen such as an outer membrane protein of one or more *Shigella* spp. In some embodiments, the artificial Invaplex is an adjuvant for the immunogen. In some embodiments, the artificial Invaplex is present in the composition in an immunogenic amount. In some embodiments, the composition is formulated as a single dose or as several divided doses. In some embodiments, the composition is formulated for mucosal administration. In some embodiments, the composition is formulated for intranasal administration. In some embodiments, the composition is formulated for parenteral administration. In some embodiments, the composition is formulated for intramuscular administration. In some embodiments, the composition is formulated for intradermal administration. In some embodiments, the subject intended to be treated with the composition is human.

In some embodiments, the present invention provides a method for inducing an immune response in a subject, which comprises administering an immunogenic amount of an artificial Invaplex comprising one or more invasin proteins complexed with a deacylated lipopolysaccharide from a gram-negative bacterial strain or a composition thereof. In some embodiments, the one or more invasin proteins are of a *Shigella* spp. In some embodiments, the deacylated lipopolysaccharide lacks one or more fatty acid chains as compared to the corresponding wild-type lipopolysaccharide. In some embodiments, the deacylated lipopolysaccharide lacks one fatty acid chain as compared to the corresponding wild-type lipopolysaccharide. In some embodiments, the deacylated lipopolysaccharide lacks two fatty acid chains as compared to the corresponding wild-type lipopolysaccharide. In some embodiments, the deacylated lipopolysaccharide lacks more than two fatty acid chains as compared to the corresponding wild-type lipopolysaccharide. In some embodiments, the gram-negative bacterial strain is a strain of *Shigella* spp. In some embodiments, the *Shigella* spp. is *S. boydii, S. dysenteriae, S. flexneri*, or *S. sonnei*. In some embodiments, the *Shigella* spp. is *S. flexneri*. In some embodiments, the gram-negative bacterial strain is a *Shigella* strain. In some embodiments, the gram-negative bacterial strain is an msbB mutant strain, such as a ΔmsbB1 mutant strain, a ΔmsbB2 mutant strain, or a ΔmsbB1/ΔmsbB2 mutant strain. In some embodiments, the gram-negative bacterial strain is a strain of a *Shigella* spp. that is an msbB mutant, such as a ΔmsbB1 mutant, a ΔmsbB2 mutant, or a ΔmsbB1/ΔmsbB2 mutant. In some embodiments, the gram-negative bacterial strain is WR10, WR20, or WR30. In some embodiments, the one or more invasin proteins are IpaB and IpaC, preferably from a *Shigella* spp. In some embodiments, the deacylated lipopolysaccharide was deacylated by enzymatic treatment. In some embodiments, the deacylated lipopolysaccharide was obtained from a strain of a *Shigella* spp. that lacks one or more genes responsible for lipopolysaccharide acylation. In some embodiments, the deacylated lipopolysaccharide was obtained from a strain of a *Shigella* spp. that has a loss-of-function mutation in one or more genes responsible for lipopolysaccharide acylation. In some embodiments, the composition further comprises an immunogen such as an outer membrane protein of one or more *Shigella* spp. In some embodiments, the artificial Invaplex is an adjuvant for the immunogen. In some embodiments, the artificial Invaplex is present in the composition in an immunogenic amount. In some embodiments, the immune response is a protective immune response. In some embodiments, the immune response is a balanced Th1/Th2 response as compared to that provided by a corresponding Invaplex comprising the corresponding wild-type lipopolysaccharide instead of the deacylated lipopolysaccharide. In some embodiments, the balanced Th1/Th2 response is a protective immune response. In some embodiments, the immune response is against one or more *Shigella* spp. In some embodiments, the immune response is against *S. flexneri* and/or *S. sonnei*. In some embodiments, the immune response is against *S. flexneri*, preferably *S. flexneri* 2a. In some embodiments, the artificial Invaplex is administered mucosally. In some embodiments, the artificial Invaplex is administered intranasally. In some embodiments, the artificial Invaplex is administered parenterally. In some embodiments, the artificial Invaplex is administered intramuscularly. In some embodiments, the artificial Invaplex is administered intradermally. In some embodiments, the subject is human.

In some embodiments, the present invention provides use of an artificial Invaplex comprising one or more invasin proteins complexed with a deacylated lipopolysaccharide from a gram-negative bacterial strain or a composition thereof for inducing an immune response in a subject. In some embodiments, the one or more invasin proteins are of a *Shigella* spp. In some embodiments, the amount of the artificial Invaplex is an immunogenic amount. In some embodiments, the deacylated lipopolysaccharide lacks one or more fatty acid chains as compared to the corresponding wild-type lipopolysaccharide. In some embodiments, the deacylated lipopolysaccharide lacks one fatty acid chain as compared to the corresponding wild-type lipopolysaccharide. In some embodiments, the deacylated lipopolysaccharide lacks two fatty acid chains as compared to the corresponding wild-type lipopolysaccharide. In some embodiments, the deacylated lipopolysaccharide lacks more than two fatty acid chains as compared to the corresponding wild-type lipopolysaccharide. In some embodiments, the gram-negative bacterial strain is a strain of *Shigella* spp. In some embodiments, the *Shigella* spp. is *S. boydii, S. dysenteriae, S. flexneri*, or *S. sonnei*. In some embodiments, the *Shigella* spp. is *S. flexneri*. In some embodiments, the gram-negative bacterial strain is a *Shigella* strain. In some embodiments, the gram-negative bacterial strain is an msbB mutant strain, such as a ΔmsbB1 mutant strain, a ΔmsbB2 mutant strain, or a ΔmsbB1/ΔmsbB2 mutant strain. In some embodiments, the gram-negative bacterial strain is a strain of a *Shigella* spp. that is an msbB mutant, such as a ΔmsbB1 mutant, a ΔmsbB2 mutant, or a ΔmsbB1/ΔmsbB2 mutant. In some embodiments, the gram-negative bacterial strain is WR10, WR20, or WR30. In some embodiments, the one or more invasin proteins are IpaB and IpaC, preferably from a *Shigella* spp. In some embodiments, the deacylated lipopolysaccharide was deacylated by enzymatic treatment. In some embodiments, the deacylated lipopolysaccharide was obtained from a strain of a *Shigella* spp. that lacks one or more genes responsible for lipopolysaccharide acylation. In some embodiments, the deacylated lipopolysaccharide was obtained from a strain of a *Shigella* spp. that has a loss-of-function mutation in one or more genes responsible for lipopolysaccharide acylation. In some embodiments, the composition further comprises an immunogen such as an outer membrane protein of one or more *Shigella* spp. In some embodiments, the artificial Invaplex is an adjuvant for the immunogen. In some embodiments, the artificial Invaplex is present in the composition in an immunogenic amount. In some embodiments, the immune response is a protective immune response. In some embodiments, the immune response is a balanced Th1/Th2 response as compared to that provided by a corresponding Invaplex comprising the corresponding wild-type lipopolysaccharide instead of the deacylated lipopolysaccharide. In some embodiments, the balanced Th1/Th2 response is a protective immune response. In some embodiments, the immune response is against one or more *Shigella* spp. In some embodiments, the immune response is against *S. flexneri* and/or *S. sonnei*. In some embodiments, the immune response is against *S. flexneri*, preferably *S. flexneri* 2a. In some embodiments, the subject is human.

In some embodiments, the present invention provides a method of immunizing a subject against one or more *Shigella* spp., which comprises administering to the subject an immunogenic amount of an artificial Invaplex according to paragraph [0010] or a composition according to paragraph [0011] by mucosal administration. In some embodiments, the subject is human.

In some embodiments, the present invention provides a method of immunizing a subject against mucosal challenge by one or more *Shigella* spp., which comprises administering to the subject an immunogenic amount of an artificial Invaplex according to paragraph [0010] or a composition according to paragraph [0011] by parenteral administration. In some embodiments, the subject is human.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description explain the principles of the invention.

DESCRIPTION OF THE DRAWINGS

This invention is further understood by reference to the drawings wherein:

FIG. 13 is a table summarizing administration site induration observed at administration site 1 and 2.

FIG. 20 is a table summarizing *Shigella* antigen-specific serum IgA and IgG endpoint titers on day 35 from mice intradermally immunized with Invaplex$_{AR\text{-}WT}$ or Invaplex$_{AR\text{-}Detox}$.

FIG. 22 is a table summarizing *Shigella* antigen-specific lung wash IgG endpoint titers on day 35 from mice intradermally immunized with Invaplex$_{AR\text{-}Wt}$ or Invaplex$_{AR\text{-}Detox}$.

FIG. 23 is a table with the results of protective efficacy of intranasal immunization with Invaplex$_{AR\text{-}WT}$ or Invaplex$_{AR\text{-}Detox}$ (ΔmsbB1/2 LPS) after intrarectal challenge with wild-type *S. flexneri* 2a 2457T.

FIG. 24 is a table detailing *Shigella* LPS and Invaplex-specific serum IgA and IgG endpoint titers on day 42 from guinea pigs intranasally immunized with Invaplex$_{AR\text{-}WT}$ or Invaplex$_{AR\text{-}Detox}$ (ΔmsbB1/2 LPS).

FIG. 25 is a table with *Shigella* IpaB and IpaC-specific serum IgA and IgG endpoint titers on day 42 from guinea pigs intranasally immunized with Invaplex$_{AR\text{-}WT}$ or Invaplex$_{AR\text{-}Detox}$ (ΔmsbB1/2 LPS).

FIG. 26 is a table with *Shigella* antigen-specific ocular IgA endpoint titers on day 42 from guinea pigs intranasally immunized with Invaplex$_{AR\text{-}WT}$ or Invaplex$_{AR\text{-}Detox}$ (ΔmsbB1/2 LPS).

FIG. 27 is a table that provides *Shigella* antigen-specific fecal IgA endpoint titers on day 35 from guinea pigs intranasally immunized with Invaplex$_{AR\text{-}WT}$ or Invaplex$_{AR\text{-}Detox}$(ΔmsbB1/2 LPS).

FIG. 28 is a table summarizing the protective efficacy after ocular challenge of guinea pigs immunized either intranasally, intramuscularly or intradermally with Invaplex$_{AR\text{-}Detox}$. Guinea pigs (n=6-12/grp) were immunized on day 0, 14 and 28 with 100 μl containing either 5 or 25 μg of *S. flexneri* 2a Invaplex$_{AR\text{-}Detox}$. On day 49, guinea pigs were challenged ocularly with ~$2.0\times10^8$ cfu/eye of *S. flexneri* 2a strain 2457T.

DETAILED DESCRIPTION OF THE INVENTION

Figure 1:
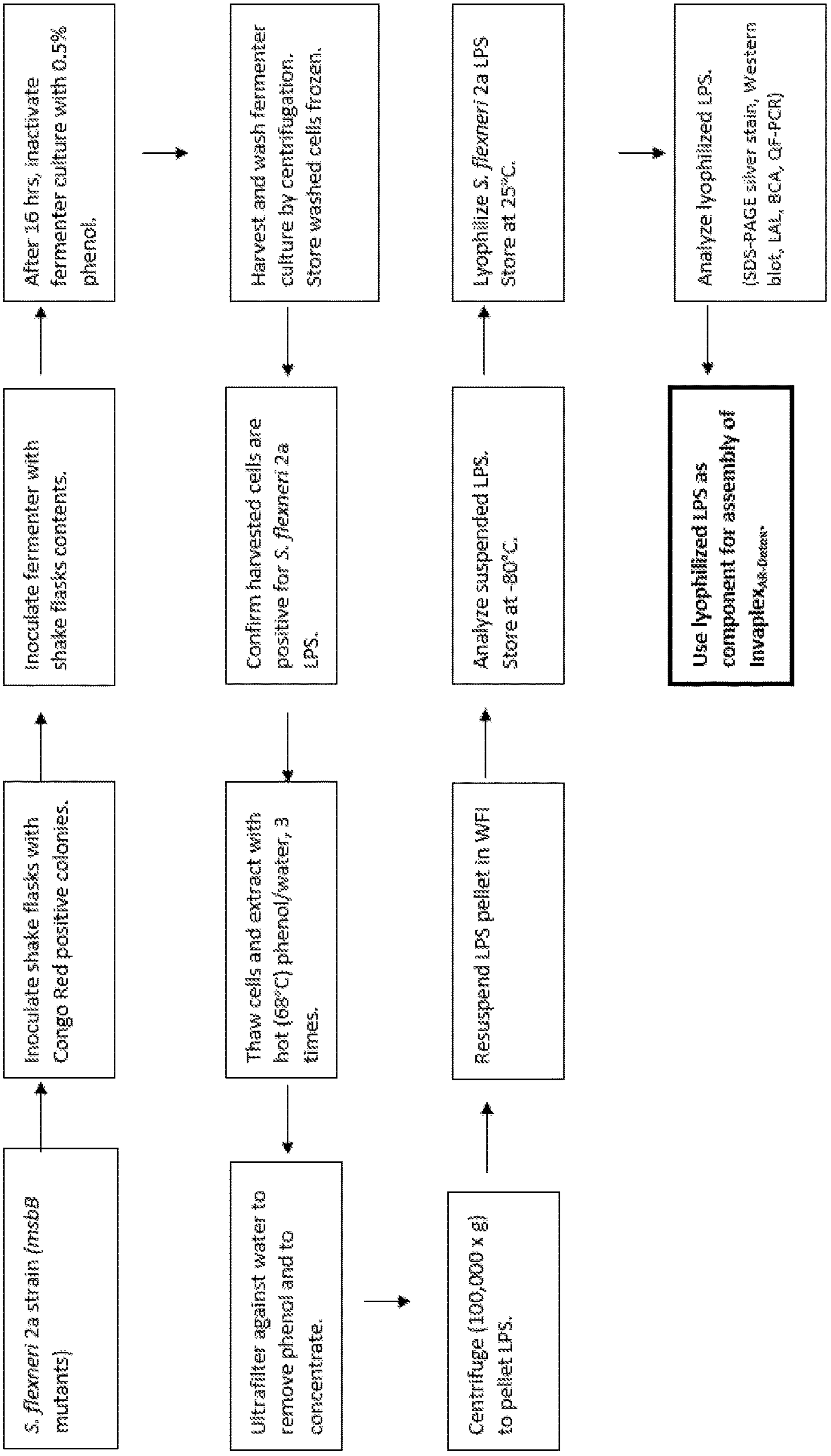
FIG. 1 is a flow diagram schematically showing the production of deacylated LPS. *S. flexneri* 2a msbB mutant strains were fermented, harvested, and washed to yield a cell paste that was phenol/water extracted to extract the LPS which was then subjected to dialysis to remove residual phenol. The dialyzed LPS was next dispensed and lyophilized to form the final LPS product used to make Invaplex$_{AR\text{-}Detox}$.

The present invention provides Invaplex$_{AR\text{-}Detox}$, which is an artificial Invaplex that contains a deacylated lipopolysaccharide (LPS), and methods of making and using thereof.

As used herein, "Invaplex$_{AR\text{-}Detox}$" refers to an artificial Invaplex made with deacylated LPS and "Invaplex$_{AR\text{-}WT}$" refers to an artificial Invaplex made with wild-type LPS (WT-LPS). As used herein, "Invaplex$_{AR}$" refers to an artificial Invaplex, i.e., a non-naturally occurring Invaplex.

As used herein, "deacylated LPS" and "detoxified LPS" are used interchangeably to refer to an LPS obtained from a gram-negative bacterium that lacks at least one fatty acid chain as compared the corresponding WT-LPS. As used herein, "wild-type LPS" refers to LPS that has been obtained from wild-type gram-negative bacteria and has not been modified such that it lacks one or more of its native fatty acid chains. In some embodiments, the deacylated LPS lacks two fatty acid chains as compared to the corresponding WT-LPS.

In some embodiments, the gram-negative bacterium is *Shigella* spp., e.g., *S. boydii, S. dysenteriae, S. flexneri*, and *S. sonnei*. In some embodiments, the gram-negative bacterium is a strain of *Shigella*. In some embodiments, the gram-negative bacterium is a strain of *Shigella flexneri* 2a. In some embodiments, the deacylated LPS is obtained from an msbB mutant. As used herein, an "msbB mutant" refers to a gram-negative bacterium that has been mutated to contain at least one defective msbB gene such that the LPS produced therefrom is missing at least one fatty acid chain as compared to that produced by the corresponding wild-type bacteria.

In some embodiments, the msbB mutant is a ΔmsbB1 (WR10), ΔmsbB2 (WR20), or ΔmsbB1/ΔmsbB2 (WR30) mutant. The ΔmsbB1/ΔmsbB2 mutant is sometimes referred to as "ΔmsbB1/2 mutant" or a "double mutant". In some embodiments, the msbB mutant is a mutant strain of *Shigella*. In some embodiments, the msbB mutant is a mutant strain of *Shigella flexneri* 2a. In some embodiments, the *Shigella* strain is WR10, WR20, or WR30.

$\text{Invaplex}_{AR\text{-}Detox}$ according to the present invention can be used as an alternative to artificial invasin complex employed in compositions and methods in the art, e.g., WO 2008118118 and *Shigella flexneri* 2a $\text{Invaplex}_{AR}$ which is in clinical trials for intranasally vaccinating against Shigellosis Bacillary Dysentery (Clinical Trial No. NCT02445963).

As disclosed herein, $\text{Invaplex}_{AR\text{-}Detox}$ is less reactogenic than $\text{Invaplex}_{AR\text{-}WT}$ after parenteral administration, yet the immunogenicity of $\text{Invaplex}_{AR\text{-}Detox}$ is similar to that of $\text{Invaplex}_{AR\text{-}WT}$. $\text{Invaplex}_{AR\text{-}Detox}$ provides a more balanced Th1/Th2 immune response as compared to that of $\text{Invaplex}_{AR\text{-}WT}$. As such, $\text{Invaplex}_{AR\text{-}Detox}$ may be more useful as a parenteral vaccine and more compatible with adjuvants as compared with $\text{Invaplex}_{AR\text{-}WT}$. Additionally, because of its reduced reactogenicity, $\text{Invaplex}_{AR\text{-}Detox}$ may be administered to subjects in amounts higher than $\text{Invaplex}_{AR\text{-}WT}$ that are typically administered, and thereby provide a more potent immune response or reduce potential reactogenicity to a level that would allow the addition of an adjuvant, which may have reactogenicity, to increase the immune response.

Therefore, in some embodiments, the present invention provides $\text{Invaplex}_{AR\text{-}Detox}$ as a vaccine. In some embodiments, the present invention provides an immunogenic composition which comprises at least one $\text{Invaplex}_{AR\text{-}Detox}$ as the immunogen. In some embodiments, the present invention provides a vaccine composition which comprises at least one $\text{Invaplex}_{AR\text{-}Detox}$ as an adjuvant. In some embodiments, the present invention is directed to vaccinating a subject against dysentery by administering to the subject an $\text{Invaplex}_{AR\text{-}Detox}$. In some embodiments, the present invention is directed to a method of inducing a balanced Th1/Th2 immune response in a subject which comprises administering at least one $\text{Invaplex}_{AR\text{-}Detox}$ to the subject. In some embodiments, the at least one $\text{Invaplex}_{AR\text{-}Detox}$ is parenterally administered to the subject. In some embodiments, the at least one $\text{Invaplex}_{AR\text{-}Detox}$ is mucosally administered to the subject. In some embodiments, the present invention provides an improvement to $\text{Invaplex}_{AR\text{-}WT}$, wherein the improvement is a deacylated LPS as a substitute for the WT-LPS in the $\text{Invaplex}_{AR\text{-}WT}$.

Compositions of the present invention, including pharmaceutical compositions and vaccines, include at least one $\text{Invaplex}_{AR\text{-}Detox}$. The term "pharmaceutical composition" refers to a composition suitable for pharmaceutical use in a subject. A pharmaceutical composition generally comprises an effective amount of an active agent, e.g., at least one $\text{Invaplex}_{AR\text{-}Detox}$ according to the present invention, and a pharmaceutically acceptable carrier. The term "effective amount" refers to a dosage or amount sufficient to produce a desired result. The desired result may comprise an objective or subjective improvement in the recipient of the dosage or amount, e.g., long-term survival, effective prevention of a disease state, and the like.

At least one $\text{Invaplex}_{AR\text{-}Detox}$ according to the present invention may be administered, preferably in the form of pharmaceutical compositions, to a subject. Preferably the subject is mammalian, more preferably, the subject is human. Preferred pharmaceutical compositions are those comprising at least one $\text{Invaplex}_{AR\text{-}Detox}$ in a therapeutically effective amount or an immunogenic amount, and a pharmaceutically acceptable vehicle.

Vaccines according to the present invention provide a protective immune response when administered to a subject. As used herein, a "vaccine" according to the present invention is a pharmaceutical composition that comprises an immunogenic amount of at least one $\text{Invaplex}_{AR\text{-}Detox}$ and provides a protective immune response when administered to a subject. The protective immune response may be complete or partial, e.g., a reduction in symptoms as compared with an unvaccinated subject. In some embodiments, a vaccine according to the present invention provides a subject with a protective immune response against infection by a *Shigella* spp., e.g., *S. boydii, S. dysenteriae, S. flexneri*, and *S. sonnei*. In some embodiments, a vaccine according to the present invention inhibits or reduces the degree of infection by a *Shigella* spp., e.g., *S. boydii, S. dysenteriae, S. flexneri*, and *S. sonnei* in a subject when administered to the subject.

As used herein, an "immunogenic amount" is an amount that is sufficient to elicit an immune response in a subject and depends on a variety of factors such as the immunogenicity of the given immunogen, the degree of infection, the manner of administration, the general state of health of the subject, and the like. Typical immunogenic amounts for initial and boosting immunizations for therapeutic or prophylactic administration may range from about 0.1 μg to 10 mg per kilogram of body weight of a subject of at least one $\text{Invaplex}_{AR\text{-}Detox}$. In some embodiments, the immunogenic amount for initial and boosting immunization for therapeutic or prophylactic administration for a human subject of 70 kg body weight ranges from about 5 μg to about 1 mg of at least one $\text{Invaplex}_{AR\text{-}Detox}$. In some embodiments, the immunogenic amount for initial and boosting immunization for therapeutic or prophylactic administration for a human subject of 70 kg body weight ranges from about 10-500 μg of at least one $\text{Invaplex}_{AR\text{-}Detox}$. In some embodiments, the immunogenic amount for initial and boosting immunization for therapeutic or prophylactic administration for a human subject of 70 kg body weight ranges from about 40-60 μg of at least one $\text{Invaplex}_{AR\text{-}Detox}$. In some embodiments, the immunogenic amount for initial and boosting immunization for therapeutic or prophylactic administration for a human subject of 70 kg body weight ranges from about 200-300 μg of at least one $\text{Invaplex}_{AR\text{-}Detox}$. In some embodiments, the immunogenic amount for initial and boosting immunization for therapeutic or prophylactic administration for a human subject of 70 kg body weight ranges from about 450-550 μg of at least one $Invaplex_{AR\text{-}Detox}$. Examples of suitable immunization protocols include an initial immunization injection (time 0), followed by booster injections at 2 and 4 weeks, which these initial immunization injections may be followed by further booster injections at 1 or 2 years if needed.

As used herein, a "therapeutically effective amount" refers to an amount that may be used to treat, prevent, or inhibit a given disease or condition, such as infection by a *Shigella* spp., in a subject as compared to a control. Again, the skilled artisan will appreciate that certain factors may influence the amount required to effectively treat a subject, including the degree of infection by a *Shigella* spp., previous treatments, the general health and age of the subject, and the like. Nevertheless, therapeutically effective amounts may be readily determined by methods in the art. It should be noted that treatment of a subject with a therapeutically effective amount or an immunogenic amount may be administered as a single dose or as a series of several doses. The dosages used for treatment may increase or decrease over the course of a given treatment. Optimal dosages for a given set of conditions may be ascertained by those skilled in the art using dosage-determination tests and/or diagnostic assays in the art. Dosage-determination tests and/or diagnostic assays may be used to monitor and adjust dosages during the course of treatment.

The compositions of the present invention may include an adjuvant. As used herein, an "adjuvant" refers to any substance which, when administered in conjunction with (e.g., before, during, or after) a pharmaceutically active agent, such as a $Invaplex_{AR\text{-}Detox}$ according to the present invention, aids the pharmaceutically active agent in its mechanism of action. Thus, an adjuvant in a vaccine according to the present invention is a substance that aids the at least one $Invaplex_{AR\text{-}Detox}$ in eliciting an immune response. Suitable adjuvants include incomplete Freund's adjuvant, alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, nor-MDP), N-acetylmuramyl-Lalanyl-D-isoglutaminyl-L-alanine-2-(1'-2'-dipa-lmitoyl-sn-glycero-3-hydroxyphosphoryloxy)-ethylamine (CGP 19835A, MTP-PE), and RIBI, which comprise three components extracted from bacteria, monophosphoryl lipid A, trehalose dimycolate and cell wall skeleton (NPL+TDM+CWS) in a 2% squalene/Tween 80 emulsion. The effectiveness of an adjuvant may be determined by methods in the art.

Pharmaceutical compositions of the present invention may be formulated for the intended route of delivery, including intravenous, intramuscular, intra peritoneal, subcutaneous, intraocular, intrathecal, intraarticular, intrasynovial, cisternal, intrahepatic, intralesional injection, intracranial injection, infusion, and/or inhaled routes of administration using methods known in the art. Pharmaceutical compositions according to the present invention may include one or more of the following: pH buffered solutions, adjuvants (e.g., preservatives, wetting agents, emulsifying agents, and dispersing agents), liposomal formulations, nanoparticles, dispersions, suspensions, or emulsions, as well as sterile powders for reconstitution into sterile injectable solutions or dispersions. The compositions and formulations of the present invention may be optimized for increased stability and efficacy using methods in the art. See, e.g., Carra et al. (2007) Vaccine 25:4149-4158, which is herein incorporated by reference.

The compositions of the present invention may be administered to a subject by any suitable route including oral, transdermal, subcutaneous, intranasal, inhalation, intramuscular, and intravascular administration. It will be appreciated that the preferred route of administration and pharmaceutical formulation will vary with the condition and age of the subject, the nature of the condition to be treated, the therapeutic effect desired, and the particular $Invaplex_{AR\text{-}Detox}$ used.

As used herein, a "pharmaceutically acceptable vehicle" or "pharmaceutically acceptable carrier" are used interchangeably and refer to solvents, dispersion media, coatings, antibacterial and antifungal agents, isotonic and absorption delaying agents, and the like, that are compatible with pharmaceutical administration and comply with the applicable standards and regulations, e.g., the pharmacopeial standards set forth in the United States Pharmacopeia and the National Formulary (USP-NF) book, for pharmaceutical administration. Thus, for example, unsterile water is excluded as a pharmaceutically acceptable carrier for, at least, intravenous administration. Pharmaceutically acceptable vehicles include those known in the art. See, e.g., REMINGTON: THE SCIENCE AND PRACTICE OF PHARMACY. $20^{th}$ ed. (2000) Lippincott Williams & Wilkins. Baltimore, Md., which is herein incorporated by reference.

The pharmaceutical compositions of the present invention may be provided in dosage unit forms. As used herein, a "dosage unit form" refers to physically discrete units suited as unitary dosages for the subject to be treated; each unit containing a predetermined quantity of the one or more $Invaplex_{AR\text{-}Detox}$ calculated to produce the desired therapeutic effect in association with the required pharmaceutically acceptable carrier. The specification for the dosage unit forms of the invention are dictated by and directly dependent on the unique characteristics of the given $Invaplex_{AR\text{-}Detox}$ and desired therapeutic effect to be achieved, and the limitations inherent in the art of compounding such an active compound for the treatment of individuals.

Toxicity and therapeutic efficacy of an $Invaplex_{AR\text{-}Detox}$ according to the instant invention and compositions thereof can be determined using cell cultures and/or experimental animals and pharmaceutical procedures in the art. For example, one may determine the lethal dose, $LC_{50}$ (the dose expressed as concentration×exposure time that is lethal to 50% of the population) or the $LD_{50}$ (the dose lethal to 50% of the population), and the $ED_{50}$ (the dose therapeutically effective in 50% of the population) by methods in the art. The dose ratio between toxic and therapeutic effects is the therapeutic index and it can be expressed as the ratio $LD_{50}/ED_{50}$. An $Invaplex_{AR\text{-}Detox}$ that exhibits large therapeutic indices is preferred. While an $Invaplex_{AR\text{-}Detox}$ that results in toxic side-effects may be used, care should be taken to design a delivery system that targets such compounds to the site of treatment to minimize potential damage to uninfected cells and, thereby, reduce side-effects.

The data obtained from the cell culture assays and animal studies can be used in formulating a range of dosages for use in humans. Preferred dosages provide a range of circulating concentrations that include the $ED_{50}$ with little or no toxicity. The dosage may vary depending upon the dosage form employed and the route of administration utilized. Therapeutically effective amounts and dosages of at least one $Invaplex_{AR\text{-}Detox}$ according to the present invention can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. Additionally, a dosage suitable for a given subject can be determined by an attending physician or qualified medical practitioner, based on various clinical factors.

In some embodiments, the present invention is directed to kits which comprise at least one Invaplex$_{AR\text{-}Detox}$, optionally in a composition, packaged together with one or more reagents or drug delivery devices for preventing, inhibiting, reducing, or treating infection by a *Shigella* spp. in a subject. Such kits include a carrier, package, or container that may be compartmentalized to receive one or more containers, such as vials, tubes, and the like. In some embodiments, the kits optionally include an identifying description or label or instructions relating to its use. In some embodiments, the kits comprise the at least one Invaplex$_{AR\text{-}Detox}$, optionally in one or more unit dosage forms, packaged together as a pack and/or in drug delivery device, e.g., a pre-filled syringe. In some embodiments, the kits include information prescribed by a governmental agency that regulates the manufacture, use, or sale of Invaplex$_{AR\text{-}Detox}$ and compositions thereof according to the present invention.

The following examples are intended to illustrate but not to limit the invention.

LPS Production

WT-LPS and deacylated LPS, obtained from *S. flexneri* 2a and msbB mutants (i.e., *S. flexneri* 2a strains having msbB deletions), were purified, lyophilized, and dried as schematically shown in FIG. 1. Then the lyophilized LPS was used to make Invaplex$_{AR\text{-}Detox}$ and Invaplex$_{AR\text{-}WT}$.

Gram-Negative Strains

The *S. flexneri* 2a wild-type and msbB mutant strains are summarized in Table 1:

TABLE 1

| Name | Genotype | Other info |
|---|---|---|
| 2457T (Wild-type) | Wild-type *S. flexneri* 2a 2457T | |
| WR10 (ΔmsbB1) | msbB1 single deletion mutant of 2457T | msbB1 is chromosomally encoded |
| WR20 (ΔmsbB2) | msbB2 single deletion mutant of 2457T | msbB2 is plasmid encoded |
| WR30 (ΔmsbB1/ΔmsbB2) | msbB1 msbB2 double deletion mutant of 2457T | |

The 2457T, WR10, WR20, and WR30 strains are described in Ranallo et al. (2010) Infect. Immun. 78:400-412. The strains 2457T, WR10, WR20, and WR30 and their LPS products are sometimes notated with “wild-type”, “ΔmsbB1”, “ΔmsbB2”, and “ΔmsbB1/ΔmsbB2”, respectively. ΔmsbB1/ΔmsbB2 is sometimes shortened to “ΔmsbB1/2”. Cell banks for each strain were prepared and stored frozen. Strains lacking msbB (late acyltransferase) have reduced lipid A acylation which reduces the net toxicity of the LPS. The *S. flexneri* msbB mutant strains, make an underacylated (i.e., deacylated) LPS with either a tetra or penta-acylated rather than a hexa-acylated lipid A as found in WT-LPS.

Production of Artificial Invaplex

Figure 2:
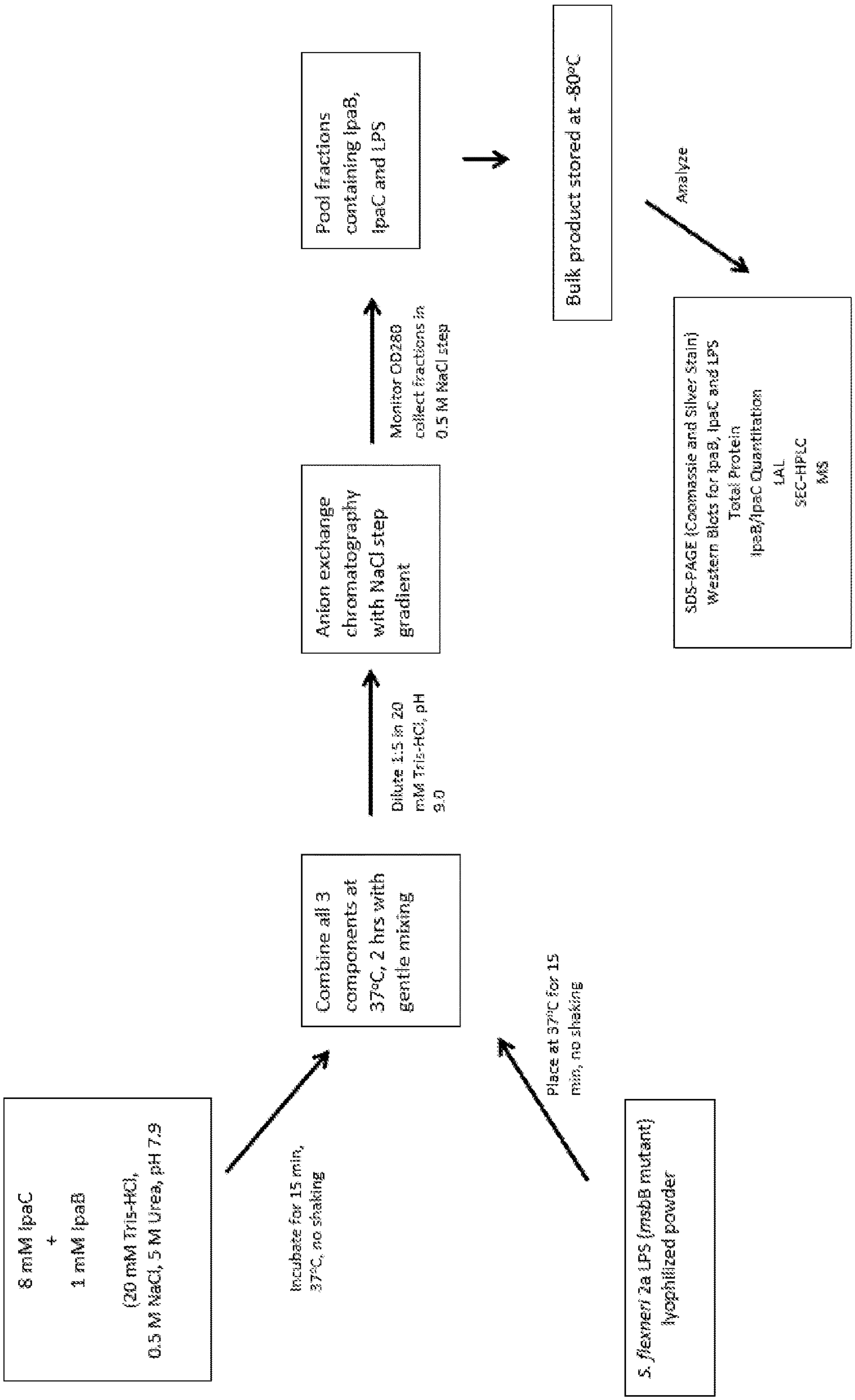
FIG. 2 is a flow diagram showing the final assembly process in which IpaB, IpaC, and deacylated LPS are combined to form a high molecular mass complex that is purified by ion-exchange chromatography.

Each artificial Invaplex was assembled from purified, recombinant IpaB, IpaC, and purified deacylated LPS from the desired species of *Shigella*, mixed in a molar ratio of 8 IpaC to 1 IpaB, and with an LPS total protein mixing ratio of approximately 2.2. FIG. 2 schematically shows the final assembly process in which IpaB, IpaC, and deacylated LPS are combined to form a high molecular mass complex that is purified by ion-exchange chromatography. Fractions containing IpaB, IpaC, and deacylated LPS are pooled and stored at −80° C. for evaluation.

Analysis of Invaplex$_{AR\text{-}Detox}$ and Invaplex$_{AR\text{-}WT}$

As it was unknown whether the deacylated LPS would prevent the formation of Invaplex, once each assembled Invaplex was purified by ion-exchange chromatography each was analyzed for quantity, quality, and identity of the individual components, as well as the molecular weight of the given Invaplex prior to use in animals or in vitro studies.

Four individual lots of Invaplex$_{AR}$ were manufactured using research grade, purified deacylated LPS from each msbB mutant strain or WT-LPS strain, the same research-grade, purified IpaB and IpaC, as well as the same mobile phases and mixing diluents. The 4 lots are as follows: Lot PB (ΔmsbB2), Lot PC (ΔmsbB1/ΔmsbB2), Lot PD (ΔmsbB1), and Lot PE (WT-LPS). Characteristics of the four Invaplex$_{AR}$ lots are shown in Table 2:

TABLE 2

| Product Lot (LPS Source) | Total Yield (Concentration) | Molar Ratio IpaC:IpaB | IpaC:IpaB Ratio by Densitometry | Hydrodynamic Radius by DLS | SEC-HPLC Retention (mins) | Endotoxin (EU/ml) | LPS (μg/mg Invaplex) |
|---|---|---|---|---|---|---|---|
| PB (ΔmsbB2) | 31.45 mg (1.7 mg/ml) | 36:1 | 9.2:1 | 22.9 ± 1.9 | 16.04 | $5.7 \times 10^7$ | 3353 |
| PC (ΔmsbB1/2) | 31.05 mg (2.3 mg/ml) | 25:1 | 5.7:1 | 18.2 ± 1.2 | 16.37 | $8.1 \times 10^7$ | 3522 |
| PD (ΔmsbB1) | 30.55 mg (1.3 mg/ml) | 28:1 | 8.7:1 | 23.5 ± 3.9 | 16.00 | $6.2 \times 10^7$ | 4769 |
| PE (WT-LPS) | 29.6 mg (1.6 mg/ml) | 25:1 | 6.8:1 | 26.7 ± 7.3 | 15.84 | $5.6 \times 10^7$ | 3500 |

Figure 3:
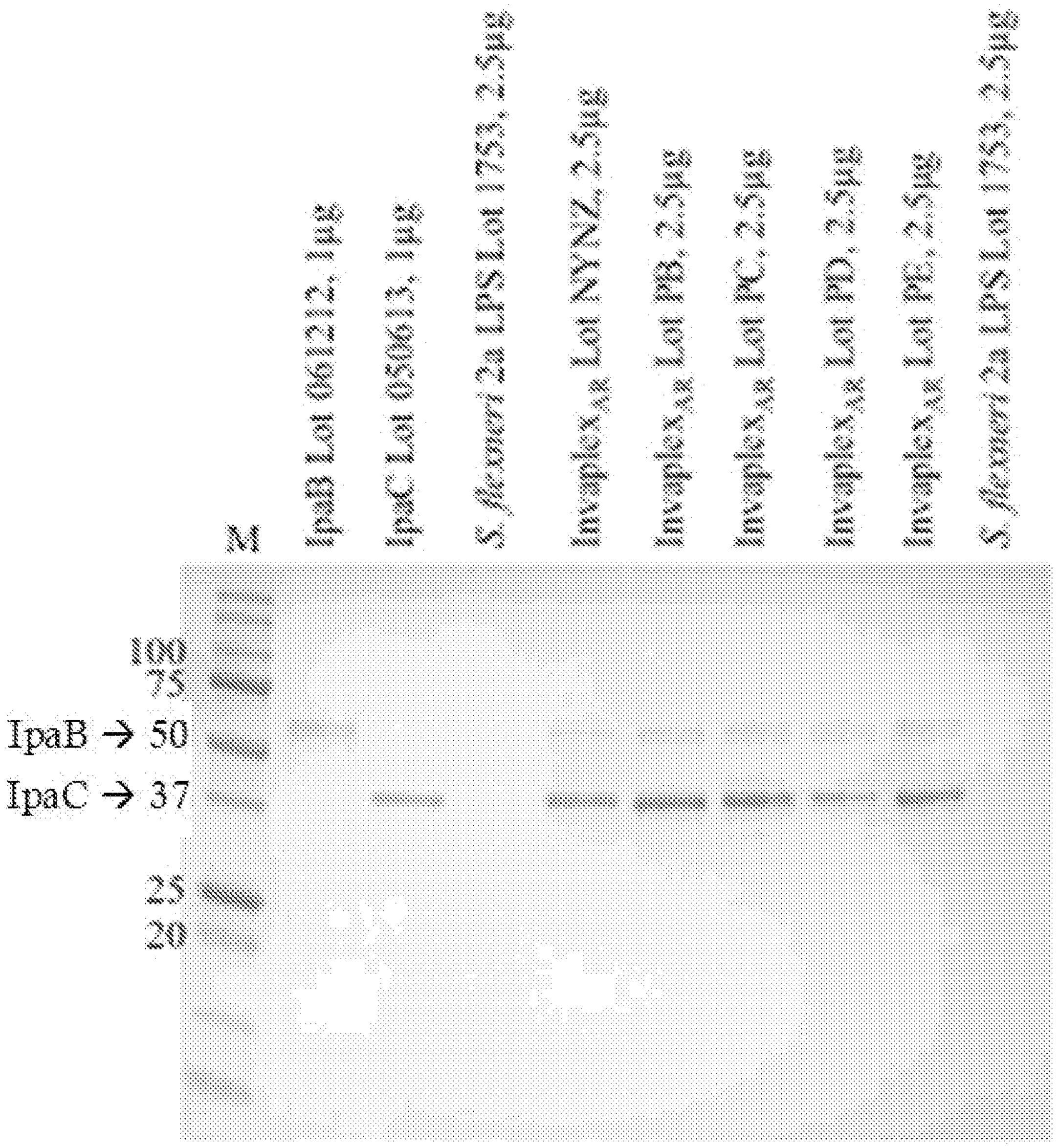
FIG. 3 is an SDS-PAGE gel of individual Invaplex$_{AR}$ components of each Invaplex exemplified herein stained with Coomassie blue.
Figure 4:
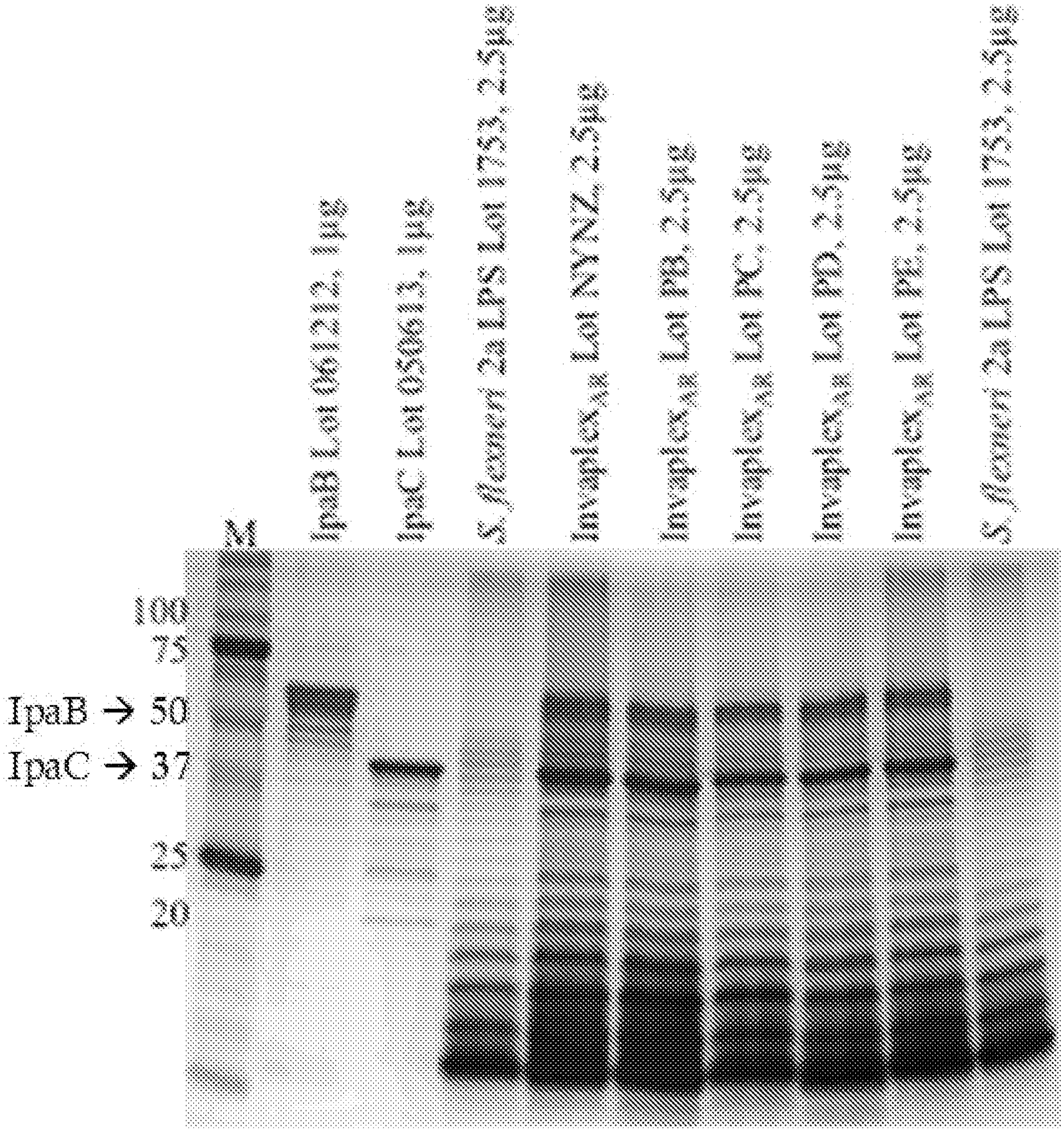
FIG. 4 is an SDS-PAGE gel of individual Invaplex$_{AR}$ components of each Invaplex exemplified herein stained with silver.

Each lot of Invaplex$_{AR-Detox}$ was found to be comparable to a reference standard, i.e., *S. flexneri* 2a Invaplex$_{AR-WT}$ Lot NYNZ, which was manufactured using similar IpaB and IpaC components and a WT-LPS-to-protein mixing ratio of 2.2. These results suggest that each Invaplex$_{AR}$ made with deacylated LPS is structurally similar to Invaplex$_{AR-WT}$. Each Invaplex formulation was analyzed by SDS-PAGE stained with Coomassie blue (FIG. 3) or silver (FIG. 4) to assess the protein and LPS content and by SEC-HPLC to estimate the size of each Invaplex$_{AR}$ complex. No differences in silver-stained LPS "ladders" were identified and all were comparable to the reference standard *S. flexneri* 2a Invaplex$_{AR}$ Lot NYNZ by SDS-PAGE analysis. SEC-HPLC showed single 215 nm peaks; however, Lots PB, PC, and PD, constructed from deacylated LPS, took slightly longer to resolve and were thus considered slightly smaller as compared to Lot PE constructed using WT-LPS. Specifically, the retention times were as follows: Lot PB=16.04 minutes, Lot PC=16.37 minutes, Lot PD=16.00 minutes, and Lot PE=15.84 minutes.

Vials of each lot were also retained for in vitro assays to measure biological function and release of pro-inflammatory cytokines from murine macrophages as well as for immunization of small animals.

MALDI-TOF Assay for Characterizing and Differentiating Deacylated LPS and WT-LPS The deacylated LPS from the WR30 (ΔmsbB1/ΔmsbB2) has one acyl group missing on the Lipid A moiety. Comparing this deacylated LPS to WT-LPS isolated from 2457T (wild-type) is difficult because the change in mass (about 210 atomic mass units, or amu) is difficult to detect by using conventional means such as gel electrophoresis.

A more sensitive assay was needed to differentiate between LPS produced from WR30 and wild-type LPS. To accomplish this task, the Lipid A from LPS samples isolated from wild-type 2457T and mutant WR30 was analyzed using MALDI-TOF mass spectrometry.

The samples were prepared for MALDI by hydrolyzing the Lipid A from the LPS samples. The LPS samples were hydrolyzed by adding 20 μl acetic acid to 180 μl of the LPS samples. The samples were heated in a heat block at 100° C. for 1 hour. The samples were then centrifuged at 12,000×g RCF for 4 minutes. The supernatant was discarded. The pellet containing the Lipid A was suspended in 5 μl of matrix solution. The matrix solution was made by dissolving 10 mg of dihydroxybenzoic acid (DHB) in 500 μl of a 1:1 ratio of WFI and HPLC grade acetonitrile. The samples were spotted on the MALDI targeting plate using the dried drop method.

Figure 29:
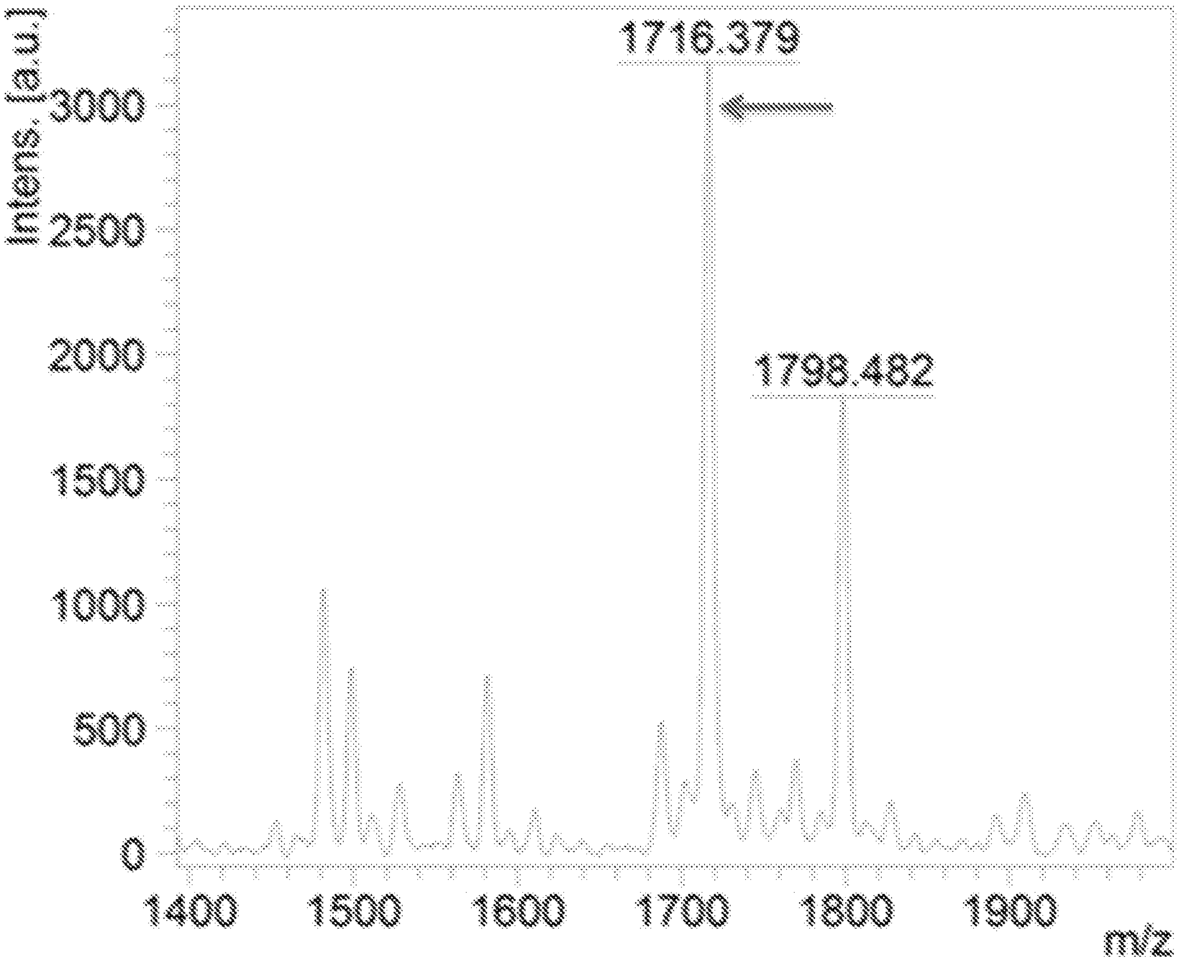
FIG. 29 is the mass spectrum of Lipid A isolated from 2457T showing a parental peak at 1798 m/z and a dephosphorylation peak at 1716 m/z (arrow).
Figure 30:
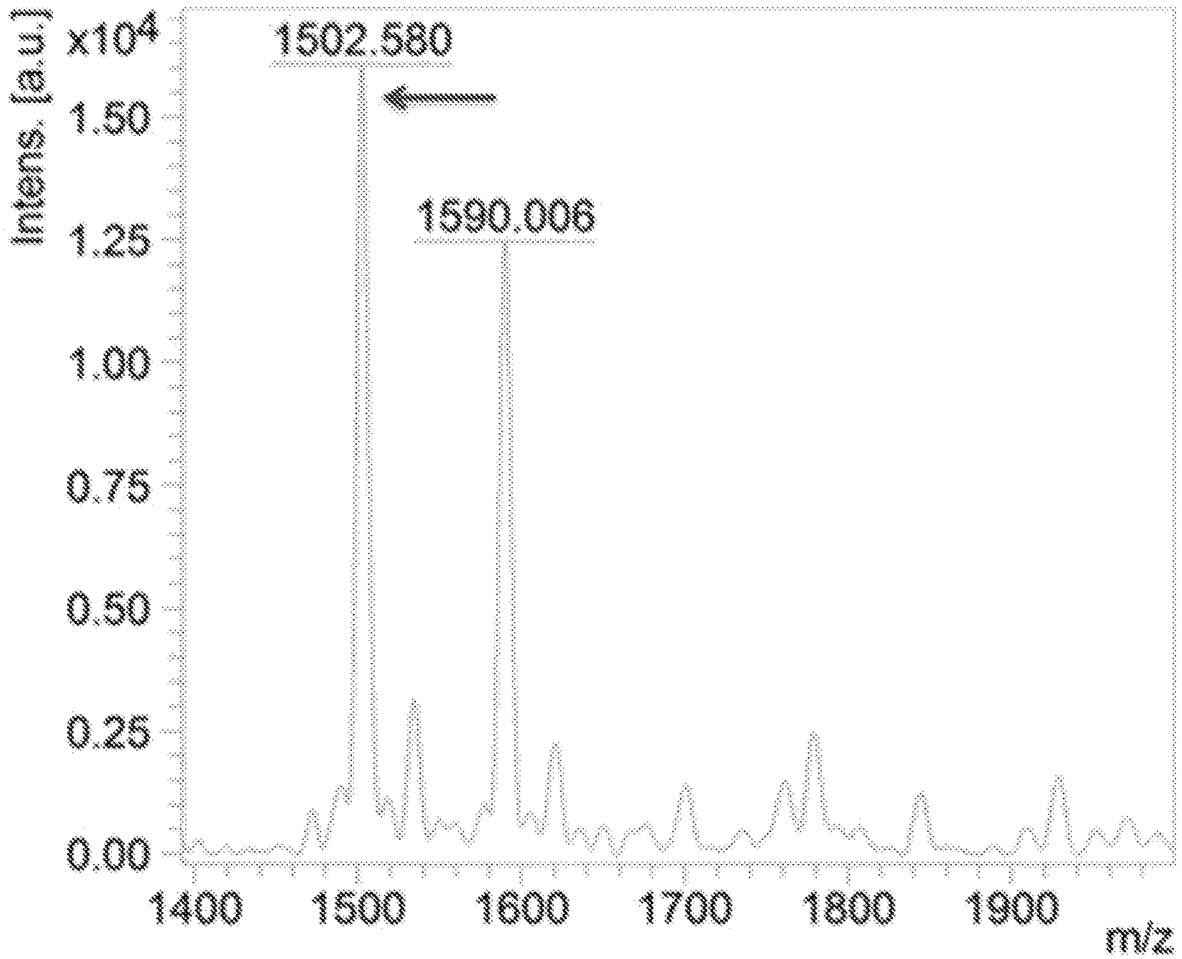
FIG. 30 is the mass spectrum of Lipid A isolated from WR30 showing a parental peak at 1590 amu and a dephosphorylation peak at 1502 amu (arrow).

The samples were analyzed on a Bruker Microflex™ MALDI-TOF instrument in the linear negative ion mode. The major peak that is the focus on both the Lipid A spectrum is the parental mass peaks. Lipid A has a theoretical molecular mass of 1798 amu. The experimentally determined mass spectrum of Lipid A isolated from 2457T shows the parental peak at 1798 m/z and a dephosphorylation peak at 1716 m/z (FIG. 29, arrow). The deacylated Lipid A of WR30 has a theoretical molecular weight of 1588 amu. The Lipid A isolated from WR30 matches the theoretical molecular weight of a deacylated Lipid A with a de-phosphorylation peak at 1502 amu (FIG. 30) and confirms the identity of the product as deacylated LPS. The experimentally determined mass spectrum lacks a peak at 1798 m/z thereby indicating that the Lipid A produced by WR30 is deacylated (FIG. 30). Mass spectrum analysis may be used to distinguish deacylated LPS from WT-LPS and thus Invaplex$_{AR-Detox}$ from Invaplex$_{AR-WT}$.

Additionally, since each Invaplex formulation contains similar quantities of IpaB, IpaC, and LPS, the use of deacylated LPS does not significantly alter the mass of the IpaB/IpaC/LPS complex, thereby indicating that a similar quantity of protein and LPS are present in the Invaplex$_{AR-WT}$ and Invaplex$_{AR-Detox}$.

Cellular Uptake of Invaplex$_{AR-Detox}$ into Fibroblasts

Since it is unknown whether Invaplex$_{AR-Detox}$ will stimulate or induce uptake by mammalian cells, the following experiment was conducted. Baby hamster fibroblast (BHK-12) cells were seeded in 8 well glass chamber slides (Nunc) and incubated overnight at 37° C. with 5% $CO_2$. Cells were washed with serum-free culture medium and incubated for 60 minutes with Lot PE (wild-type), Lot PD (ΔmsbB1), Lot PB (ΔmsbB2), or Lot PC (ΔmsbB1/2). The Invaplex$_{AR}$ preparations were diluted to 2.5, 25, and 250 g/ml in serum-free culture medium and incubated in duplicate chamber slide wells. After a 60 minute incubation at 37° C., the wells were washed 5× with PBS and fixed with 10% formalin for 30 minutes at ambient temperature (about 23° C.).

Internalized Invaplex$_{AR}$ was detected by incubating the chamber slide wells with an anti-*S. flexneri* 2a, 2457T polyclonal rabbit serum (WRAIR Rabbit #7 diluted 1:200 in 10% FCS containing 0.001% saponin). After incubation, unbound antibody was removed by washing. Bound rabbit antibodies were detected using goat anti-rabbit antibodies conjugated to Oregon Green 488 (Invitrogen; 0.5 μg/ml) and the nucleus was stained with Dapi (0.1 μg/ml).

Cells were viewed at 60× magnification on a Nikon Optiphot® fluorescent microscope. The integrity of the cells was evaluated using bright-field microscopy. The number of cells in five random fields per well were enumerated based on nuclear staining and the number of Invaplex positive cells (stained with Oregon Green) were enumerated. A minimum of 150 cells from each well were scored. The percentage of Invaplex$_{AR}$ positive cells was calculated by dividing the total number of Invaplex$_{AR}$ positive cells (Oregon Green stain) by the total number of cells (Dapi stain)

Examination by bright-field microscopy did not reveal differences between cells treated with Invaplex$_{AR-WT}$, Invaplex$_{AR-Detox}$, and cells incubated with culture medium in terms of cellular damage, rounded cells, or loss of cells. The percentage of Invaplex positive cells after incubation with various concentrations of Invaplex preparations are shown in Table 3 as follows:

TABLE 3

| Treatment | Percentage of Invaplex$_{AR}$ positive BHK-21 cells after incubation with Invaplex$_{AR-WT}$ or Invaplex$_{AR-Detox}$ diluted to: | | | |
|---|---|---|---|---|
| | 0 μg/ml | 2.5 μg/ml | 25 μg/ml | 250 μg/ml |
| Invaplex$_{AR-WT}$ (WT-LPS; Lot PE) | <1 | 9 | 44 | 93 |
| Invaplex$_{AR-Detox}$ (ΔmsbB1 LPS; Lot PD) | <1 | 31 | 30 | 74 |
| Invaplex$_{AR-Detox}$ (ΔmsbB2 LPS; Lot PB) | <1 | 23 | 15 | 84 |
| Invaplex$_{AR-Detox}$ (ΔmsbB1/2 LPS; Lot PC) | <1 | 9 | 62 | 99 |

Invaplex$_{AR}$ was found in a comparable percentage of cells incubated with Invaplex$_{AR-WT}$ or Invaplex$_{AR-Detox}$ (ΔmsbB1/2 LPS; Lot PC) across the various concentrations. At the 2.5 μg/ml concentration, a >2-fold increase in the percentage of cells identified as Invaplex$_{AR}$ positive after treatment with $Invaplex_{AR-Detox}$ (ΔmsbB1 LPS; Lot PD) and $Invaplex_{AR-Detox}$ (ΔmsbB2 LPS; Lot PB) as compared to $Invaplex_{AR-WT}$ was seen. At the 250 μg/ml concentration, ≥74% of BHK-21 cells were $Invaplex_{AR}$-positive after treatment with the various $Invaplex_{AR}$ preparations.

All three $Invaplex_{AR-Detox}$ preparations induce self-uptake in BHK-21 cells. Thus, the use of deacylated LPS to produce artificial Invaplex does not alter the native uptake activity of $Invaplex_{AR}$ and suggests $Invaplex_{AR-Detox}$ preparations may be suitable for use as vaccines, adjuvants and/or transporters.

Pro-Inflammatory Cytokine Release from Macrophages Exposed to Invaplex

Due to the known endotoxic properties of LPS from wild-type *Shigella* spp., it is probable that Invaplex made with *Shigella* WT-LPS will have endotoxic properties capable of inducing reactogenicity in parenterally immunized hosts. The potential toxicity of Invaplex products can be evaluated in vitro by using cultured cells that are sensitive to endotoxin and release pro-inflammatory cytokines such as TNF-α upon exposure to LPS. Using cultured eukaryotic cells (mouse macrophages), the toxicity of each $Invaplex_{AR}$ preparation, and the LPS used to construct each preparation was determined.

Murine macrophages (J77A.1; ATCC TIB-67) were seeded in 96 well tissue culture plates and incubated overnight at 37° C. Cells were washed with serum-free culture medium and incubated for 6 hours with LPS obtained from 2457T (wild-type), WR10, WR20, and WR30 at 1, 0.1, or 0.01 μg/ml. Other wells were incubated with a given $Invaplex_{AR}$ preparation at 1, 0.1, or 0.01 μg/ml. The LPS component to construct each $Invaplex_{AR}$ preparation was the same material used in the LPS-only experiments. After incubation for 2, 4, and 6 hours, supernatant was collected from triplicate wells and assayed by Luminex to determine TNF-α concentration.

Figure 5:
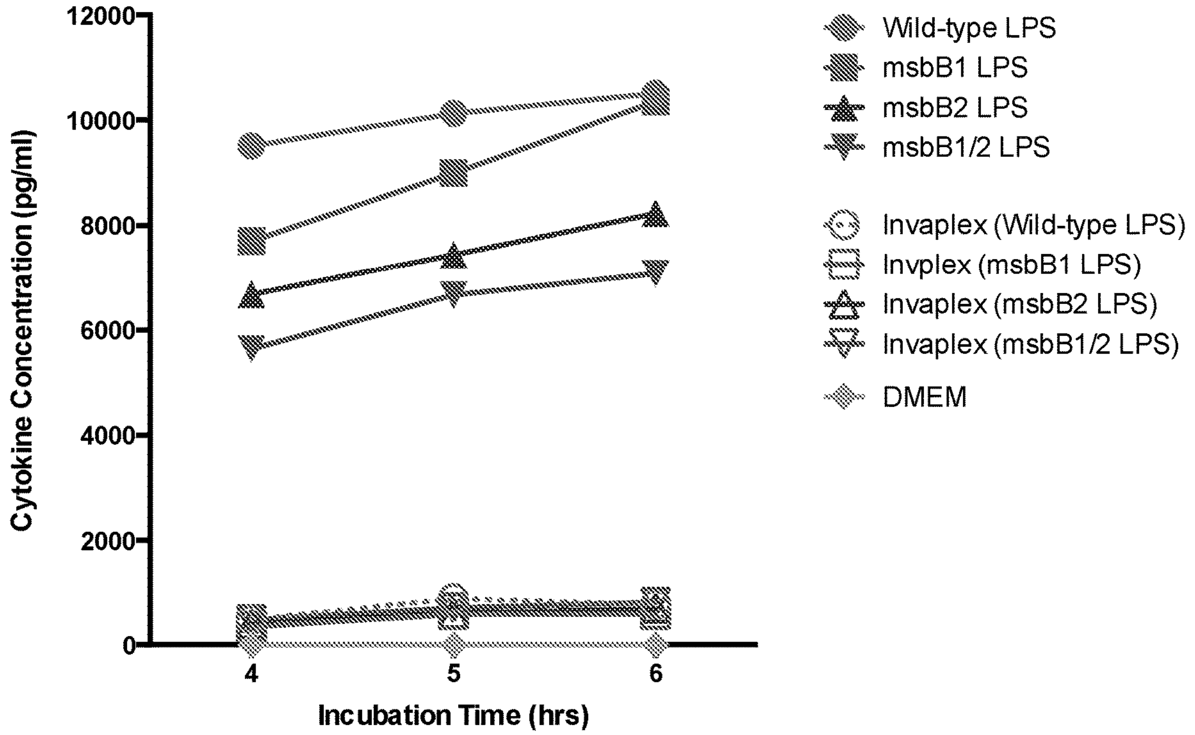
FIG. 5 is a graph showing TNF-α release from murine macrophages after incubation with 0.01 μg of LPS purified from *S. flexneri* 2a strain 2457T (wild-type), the indicated ΔmsbB mutant strain, or 0.1 μg of Invaplex preparations made therewith each given LPS.

As shown in FIG. 5, incubation of murine macrophages with WT-LPS (0.01 μg/ml) resulted in the release of robust levels of TNF-α at the 4 hour time point (mean=9507 pg/ml) and increased to 10,514 pg/ml after 6 hours. In contrast, TNF-α was low (<10 pg/ml) in the macrophage supernatant after incubation with culture medium alone (DMEM). The concentration of TNF-α in supernatants of cells incubated with LPS from any of the three ΔmsbB mutants was significantly lower as compared to TNF-α concentrations after incubation with WT-LPS at the 4 hour time point. At the 6 hour time point, TNF-α concentrations in the macrophage supernatants from cells incubated with LPS from the ΔmsbB1 mutants were comparable to the TNF-α concentration in supernatant from cells incubated with WT-LPS whereas cells incubated with LPS from ΔmsbB2 or LPS from ΔmsbB1/2 were significantly lower levels of TNF-α as compared to cells incubated with WT-LPS.

Incubation of murine macrophages with 1, 0.1, and 0.01 μg/ml of $Invaplex_{AR-WT}$ and each $Invaplex_{AR-Detox}$ resulted in release of significantly lower levels of TNF-α as compared to the purified LPS preparations. Maximal TNF-α release was 3097 pg/ml after incubation with 1 μg/ml $Invaplex_{AR-Detox}$ assembled with ΔmsbB2 LPS. Incubation of macrophages with 0.1 or 0.01 μg/ml of the $Invaplex_{AR-Detox}$ preparations caused the release of TNF-α at low concentrations (<1000 pg/ml).

Thus, murine macrophages incubated with deacylated LPS release significantly less TNF-α as compared to WT-LPS. The lowest level of TNF-α was observed in the supernatant of macrophages incubated with LPS from the double msbB mutant strain (ΔmsbB1/2). Incubation of macrophages with $Invaplex_{AR-WT}$ or $Invaplex_{AR-Detox}$ preparations significantly reduced the amount of TNF-α released into the culture supernatant, as compared to LPS-treated cells, even when 10-fold more $Invaplex_{AR-WT}$ or $Invaplex_{AR-Detox}$ was used for stimulation. Collectively, these data indicate that purified LPS from the double msbB mutant strain (ΔmsbB1/2) has the lowest potential to cause the release of pro-inflammatory cytokines. Formation of the $Invaplex_{AR}$ complex appears to further reduce the pro-inflammatory capacity of *Shigella* LPS.

As the $Invaplex_{AR-Detox}$ preparations exhibit less toxicity in vitro, $Invaplex_{AR-Detox}$ preparations have advantages over $Invaplex_{AR-WT}$, such as a reduced likelihood of inducing reactogenicity by parenteral (subcutaneous, intramuscular, intradermal, etc.) administration.

Reactogenicity of $Invaplex_{AR-Detox}$ Preparations In Vivo

The in vivo immunogenicity and reactogenicity of the $Invaplex_{AR-WT}$ and $Invaplex_{AR-Detox}$ preparations was evaluated. Groups of female CD-1 mice (5 mice/grp) were immunized intradermally (50 μl total volume) on day 0 and 21 with dose amounts of 0.25, 2.5, or 25 μg of the given $Invaplex_{AR}$ preparation described in Table 2. The control group received 0.9% sterile saline (negative control). Prior to immunization all mice were anesthetized with ketamine/rompun. At the site of immunization, each mouse was observed on days 2 and 3 after each immunization for edema, erythema, and induration. In addition, after the first immunization animal appearance and body weight were recorded as indicators of reactogenicity. On study day 35, all mice were euthanized and mucosal washes (lung and intestinal) were collected. Blood samples were collected from individual mice in each group on day 0 and 35. Blood and mucosal washes were assayed by ELISA for antigen-specific antibody endpoint titers.

Figure 6:
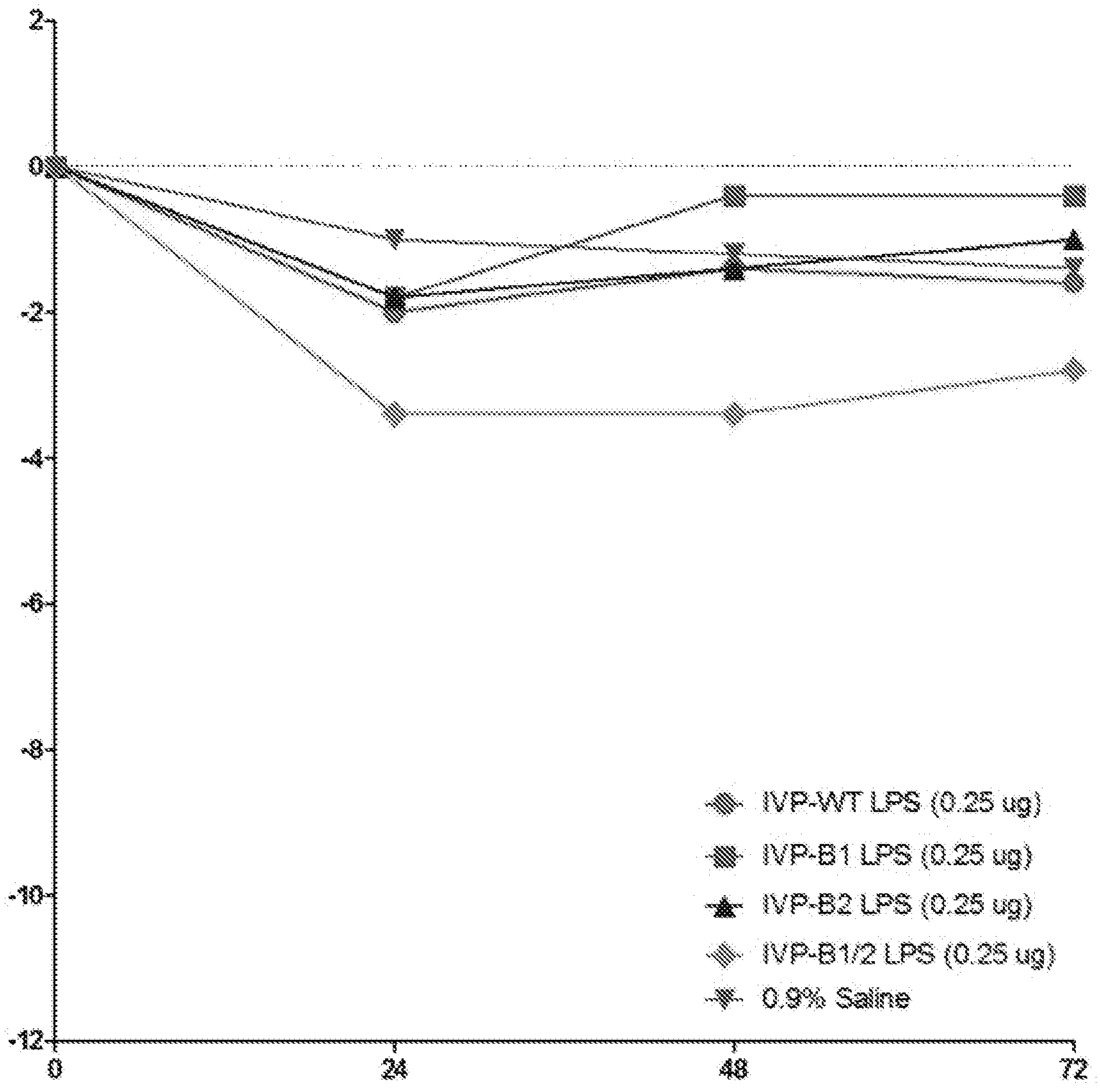
FIG. 6, FIG. 7, and FIG. 8 are graphs showing mean percent weight change of mice treated with 0.25 μg, 2.5 μg, and 25 μg, respectively, of the given Invaplex$_{AR}$ preparation or control at 24, 48, and 72 hours after each intradermal immunization.
Figure 7:
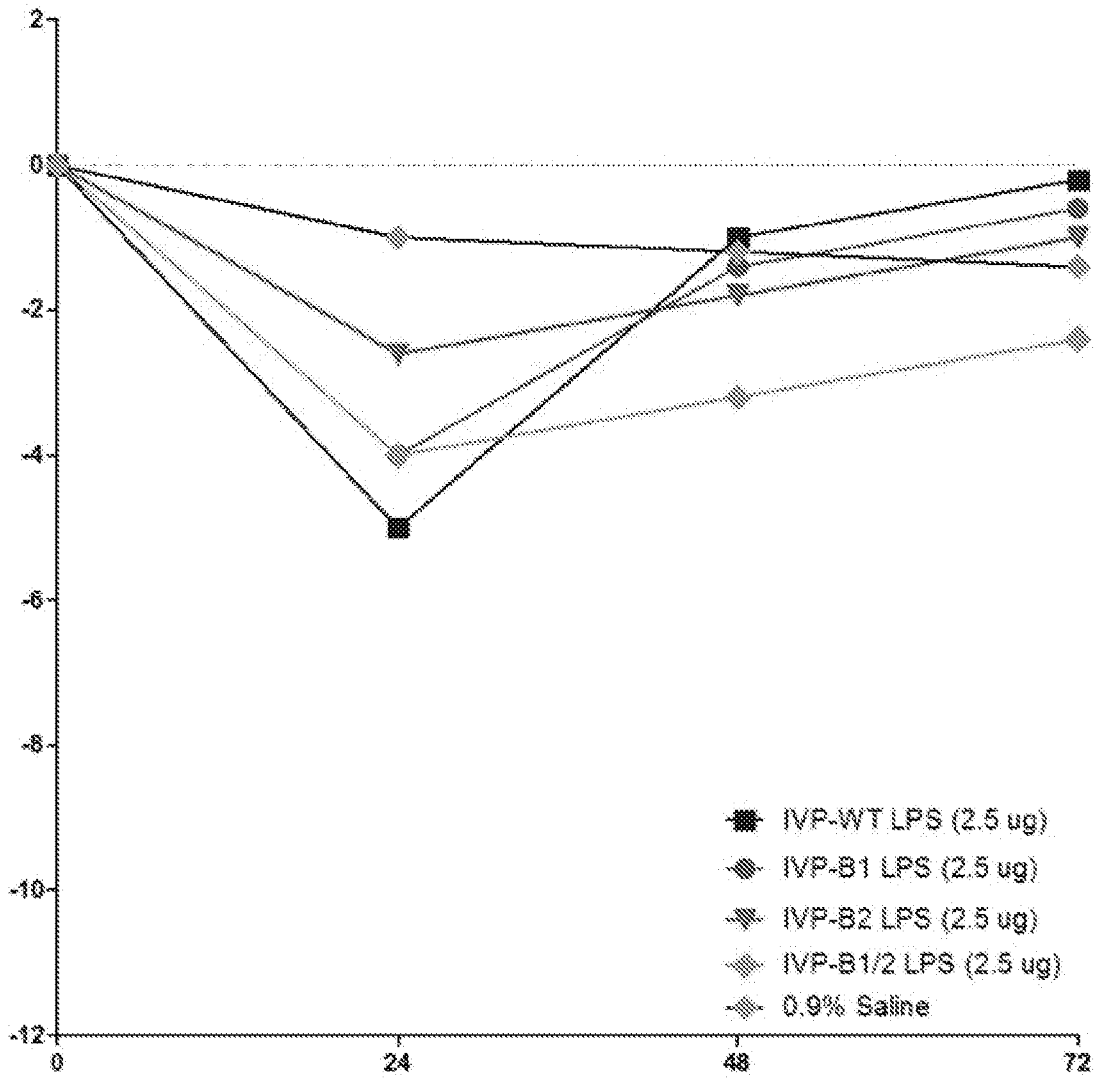
Figure 8:
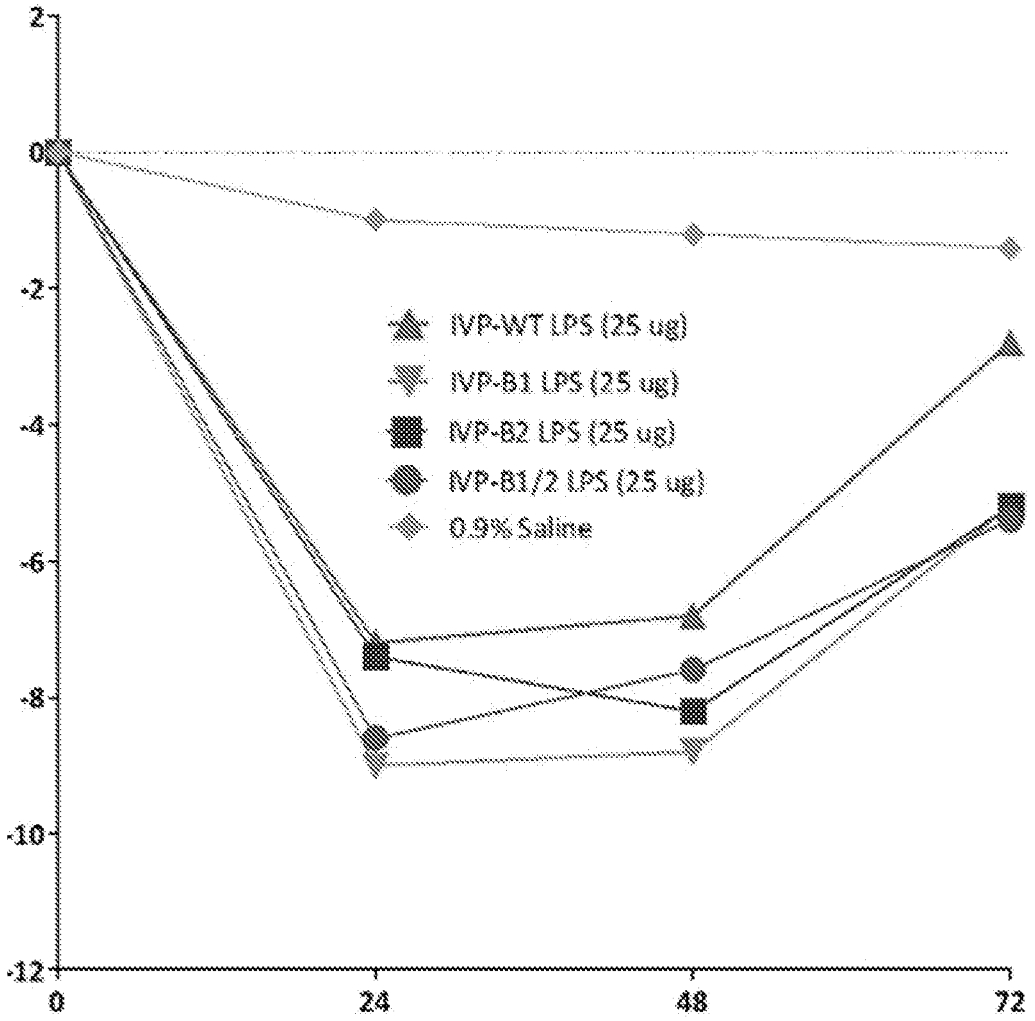

Individual mice were weighed with a calibrated scale prior to each immunization and then 24, 48, and 72 hours after each immunization. The percent weight change was calculated for individual animals at 24-hour intervals after the second immunization and the mean percent weight change was plotted for each dose group and the results are provided in FIG. 6 (0.25 μg), FIG. 7 (2.5 μg), and FIG. 8 (25 μg). There were no statistically significant differences in the percent weight change between any of the groups immunized with 0.25 or 2.5 μg of the $Invaplex_{AR}$ preparations and the control group immunized with saline (FIG. 6 and FIG. 7, respectively). In the 25 μg dose arm (FIG. 8), all groups immunized with the $Invaplex_{AR-Detox}$ preparations had weight changes that were similar to the group immunized with $Invaplex_{AR}$ containing WT-LPS. All of the $Invaplex_{AR}$-immunized groups had significantly more weight change (loss) than the group immunized with saline at 24 and 48 hours post immunization. Immunization of mice with $Invaplex_{AR-Detox}$ formulations did not result in a significant difference in terms of weight change as compared to groups immunized with $Invaplex_{AR-WT}$.

Figure 9:
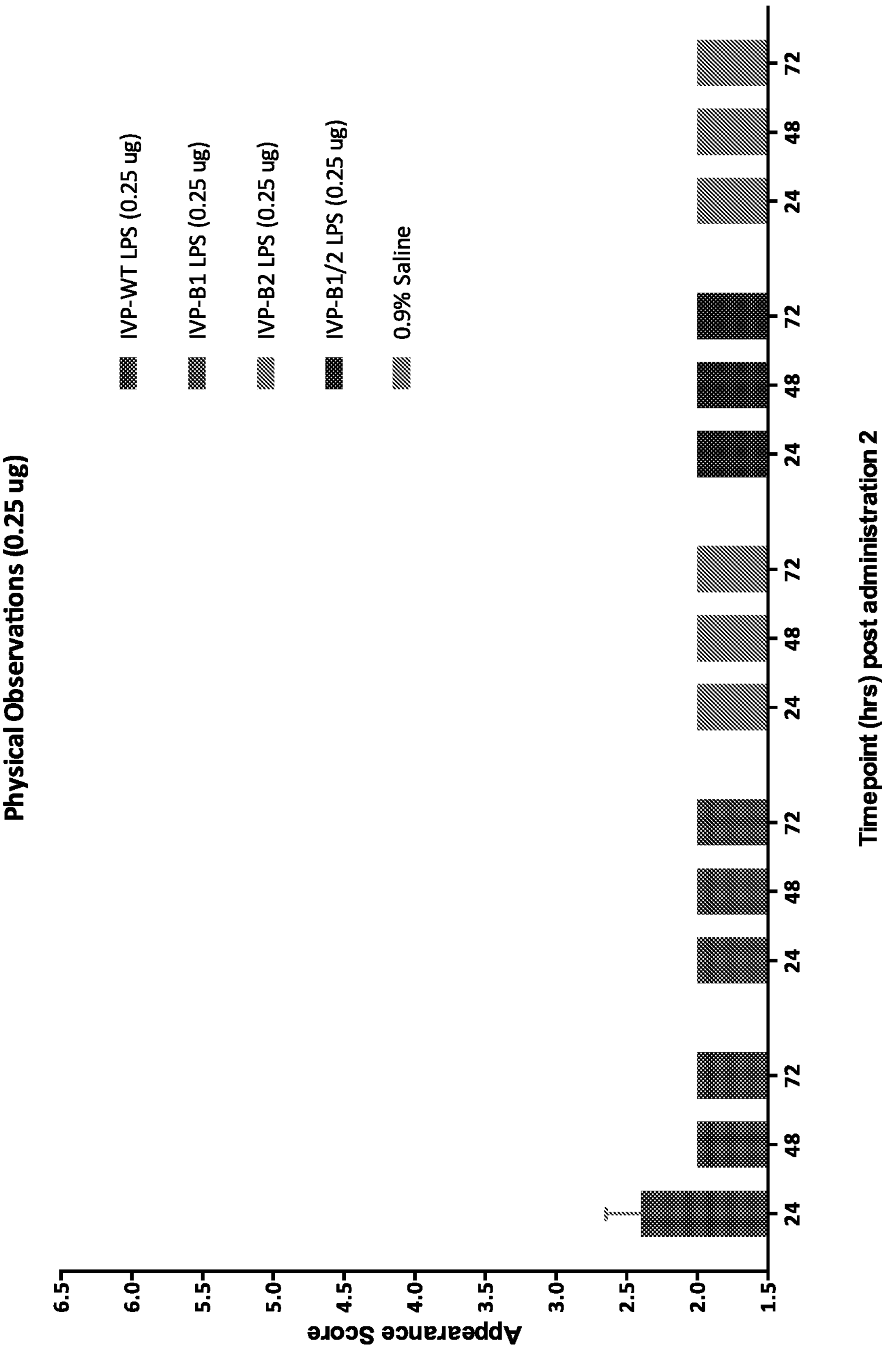
FIG. 9, FIG. 10, and FIG. 11 are graphs of the mean scores of ruffled fur and hunched posture after intradermal immunization of the group administered with 0.25 μg, 2.5 μg, and 25 μg, respectively, of the indicated Invaplex$_{AR}$ preparation at the indicated time points. As shown, the LPS of the Invaplex$_{AR}$ preparations for each set of bars in the graph from left to right are: WT-LPS, B1-LPS (from WR10), B2-LPS (from WR20), and B1/2-LPS (from WR30), and the last sets of bars are saline.
Figure 10:
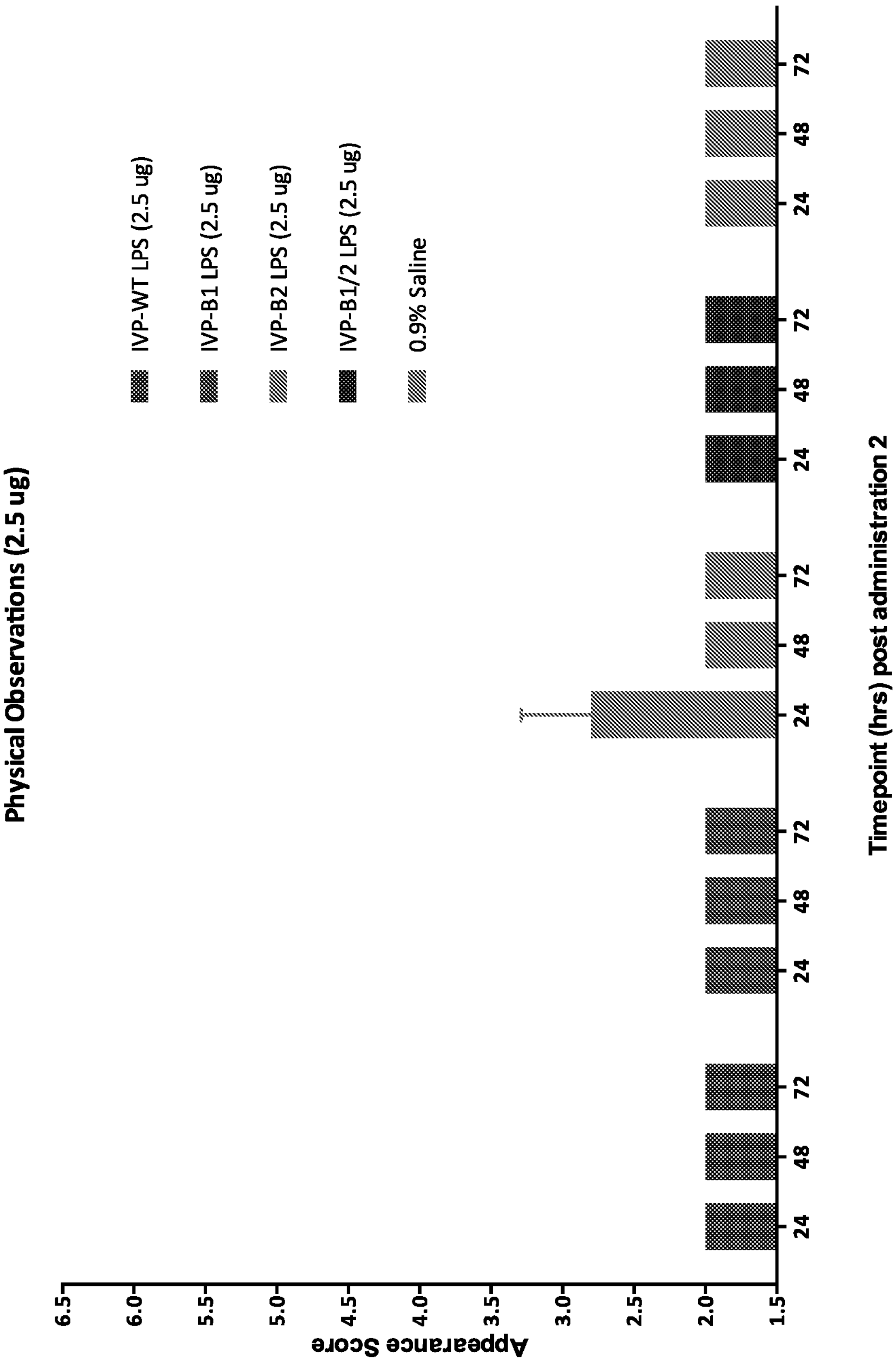
Figure 11:
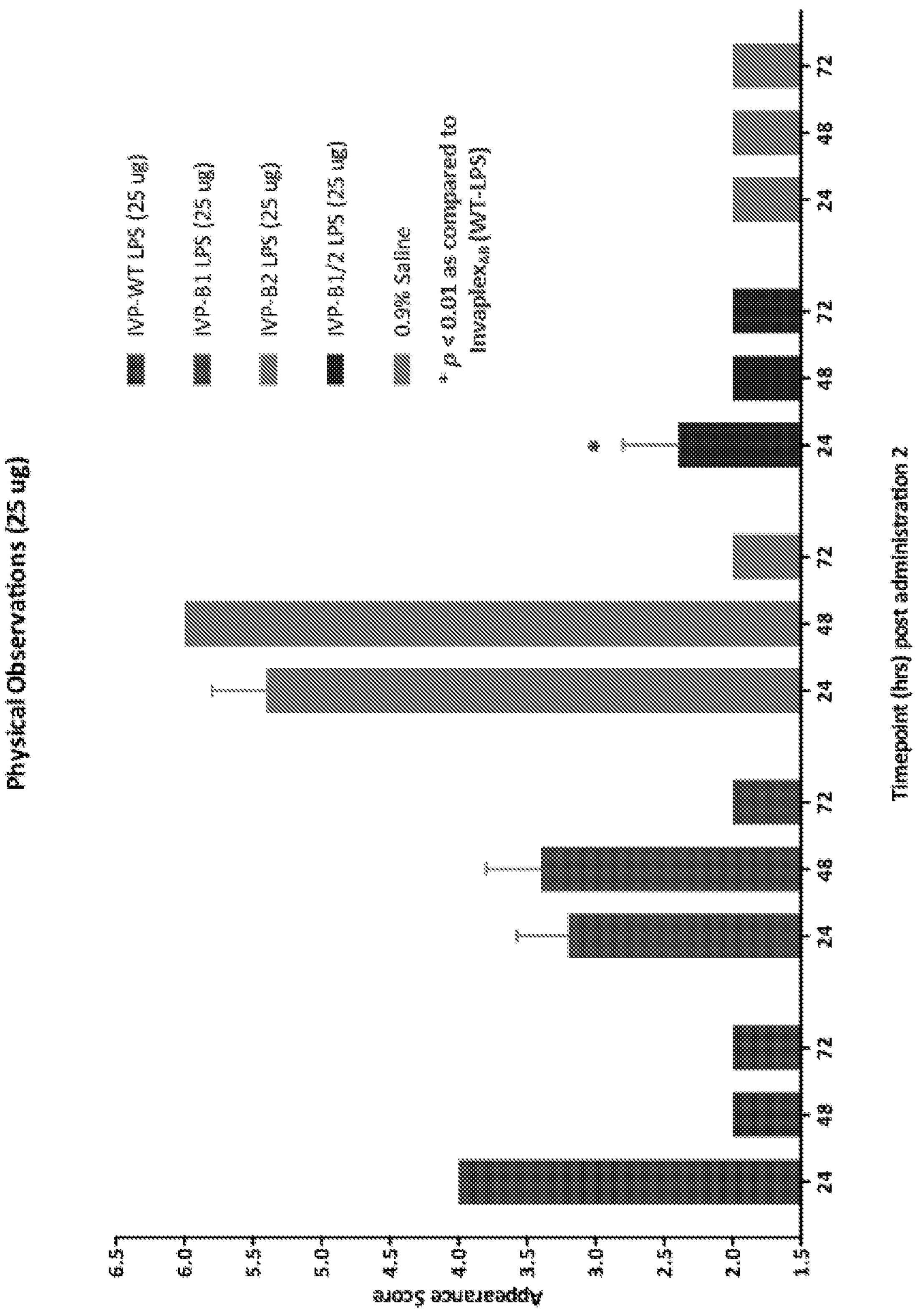

Individual mice were observed at 24, 48, and 72 hours post vaccine administration for ruffled fur and hunched posture, two physical signs of stress in the mouse model. Fur appearance was recorded as either normal, slightly ruffled, or ruffled and the posture was recorded as either normal, slightly hunched, or hunched. The observations were then assigned a numerical value based on severity on a scale of 1 to 3. A reactogenicity score was then calculated for each animal by summing the individual scores recorded for posture and physical appearance of the fur. Animals administered 0.9% saline did not exhibit fur ruffling or hunched posture at any time point. Similarly, there were minimal changes to fur and posture in groups immunized intradermally with either 0.25 μg (FIG. 9) or 2.5 μg (FIG. 10) of the Invaplex$_{AR-Detox}$ preparations. At the 25 μg dose amount, mice immunized with Invaplex$_{AR-WT}$ had slightly ruffled fur and slightly hunched postures 24 hours post administration which resolved within 48 hours (FIG. 11). Moderate levels of reactogenicity were observed after immunization with Invaplex$_{AR-Detox}$ containing LPS from ΔmsbB1 but the reactogenicity was resolved by 72 hours post administration. Minimal levels of reactogenicity were observed in mice immunized with Invaplex$_{AR-Detox}$ containing LPS from the double ΔmsbB1/2 mutant and the levels were significantly lower (ANOVA; $p<0.01$) as compared to mice immunized with Invaplex$_{AR-WT}$. The highest level of reactogenicity was observed in mice immunized with Invaplex$_{AR-Detox}$ containing LPS isolated from the ΔmsbB2 mutant. In summary, outward signs of stress (ruffled fur and hunched posture) were of minimal magnitude and duration in animals immunized with Invaplex$_{AR-Detox}$ assembled with LPS isolated from the ΔmsbB1/2 mutant.

Vaccine administration sites were observed for erythema, edema, and induration prior to vaccination and three consecutive days post each vaccination. Administration sites were graded according to a modified Draize scale for administration site monitoring in Table 4:

TABLE 4

| | Score |
|---|---|
| Erythema | |
| No erythema | 0 |
| Very slight, barely perceptible erythema (pink/red to red area) | 1 |
| Well-defined erythema (easily identifiable area of redness) | 2 |
| Moderate to severe erythema (medium to dark red) | 3 |
| Edema formation | |
| No edema | 0 |
| Very slight, barely perceptible edema, no defined edges (Raised circumference <5 mm) | 1 |
| Moderate edema-area raised approximately 1 mm (Raised circumference of 5-10 mm) | 2 |
| Severe edema-area raised more than 1 mm, extending beyond the area of exposure (Raised area >10 mm) | 3 |
| Induration | |
| No induration | 0 |
| Identifiable area of firmness | Measurements collected |
| Unable to detect induration due to edema formation | U |

Grading was conducted in a blinded manner, with the person assigning the grades unaware of the vaccine administered to the animals. Observations were conducted by a team of individuals trained on the scoring system and supervised by a board-certified veterinary pathologist. When induration was observed, measurements of the length and width of the affected tissue were recorded. The areas of induration, defined as a palpable, raised, hardened area at the administration site was calculated using the following formula:

$$\text{Calculated induration}=(0.5\times\text{length})\times(0.5\times\text{width})\times\pi$$

The length and width were measured in millimeters using calibrated calibers and π was defined as 3.14.

Erythema was undetectable in groups immunized with saline or 0.25 μg of the four Invaplex$_{AR}$ preparations used in the study (FIG. 12). Erythema was also absent in groups receiving 2.5 μg of Invaplex$_{AR-WT}$, Invaplex$_{AR-Detox}$ (ΔmsbB2 LPS), and Invaplex$_{AR-Detox}$ (ΔmsbB1/2 LPS) preparations. Low to moderate levels of erythema were observed after immunization with 25 μg of all the Invaplex$_{AR}$ preparations.

Similar to erythema results, edema was low or absent in mice immunized with saline or with 0.25 or 2.5 μg of the four Invaplex preparations (FIG. 12). Edema was most prominent in groups immunized with 25 μg dose amounts of the Invaplex$_{AR}$ preparations. In summary, mice immunized with Invaplex$_{AR-Detox}$ (ΔmsbB1/2 LPS) had the least amount of edema observed of all the formulations tested.

Induration measurements were collected on the day of each immunization and for three days following each immunization for administration site 1 and 2 (FIG. 13). In most groups, induration was absent (scored as 0). In some groups, induration was undetectable or could not be measured accurately (scored as U) due to edema formation that hindered identifying clear perimeters for induration measurement. Due to the lack of clear induration data, induration was not considered when determining reactogenicity.

Immunogenicity of Invaplex$_{AR-Detox}$ Preparations In Vivo

Mice were immunized intradermally on days 0 and 21. Blood samples were collected from individual mice in each group on day 0 and 35. On study day 35, all mice were euthanized and mucosal washes (lung and intestinal) were collected. Blood and mucosal washes were assayed by ELISA for antigen-specific antibody endpoint titers. Serum for serology was collected and processed and the serum IgG and IgA endpoint titers specific for *Shigella* antigens (LPS, native Invaplex, IpaB, and IpaC) were determined using methods in the art.

Blood collected on day 0 and 35 were analyzed by ELISA for serum IgG and IgA endpoint titers directed to *S. flexneri* 2a LPS, *S. flexneri* 2a Invaplex, IpaB, and IpaC. Antigen-specific serum IgG and IgA were undetectable in samples collected before immunization (day 0) from all mice in each treatment group. Similarly, mice immunized with saline did not have detectable (titer <180) *Shigella*-specific serum antibodies.

Figure 14:
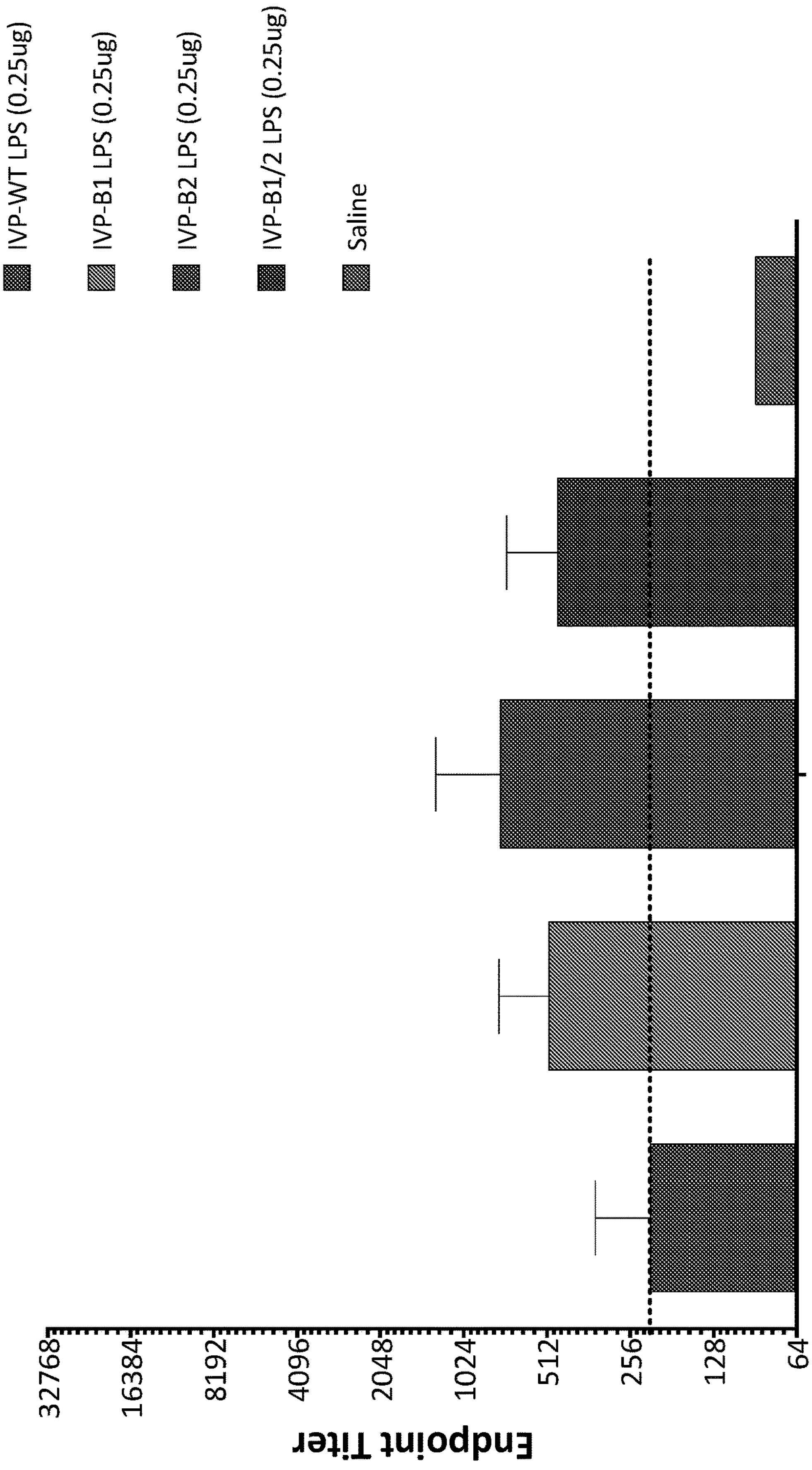
FIG. 14, FIG. 15, and FIG. 16 are graphs showing the *Shigella* LPS-specific serum IgG endpoint titers on day 35 from mice intradermally immunized with 0.25 μg, 2.5 μg, and 25 μg, respectively, of the indicated Invaplex$_{AR}$ preparation. As shown from left to right the LPS are: WT-LPS, B1-LPS (from WR10), B2-LPS (from WR20), and B1/2-LPS (from WR30), and the 5th bar is saline. Dotted lines represent GMT after immunization with Invaplex$_{AR\text{-}WT}$.
Figure 15:
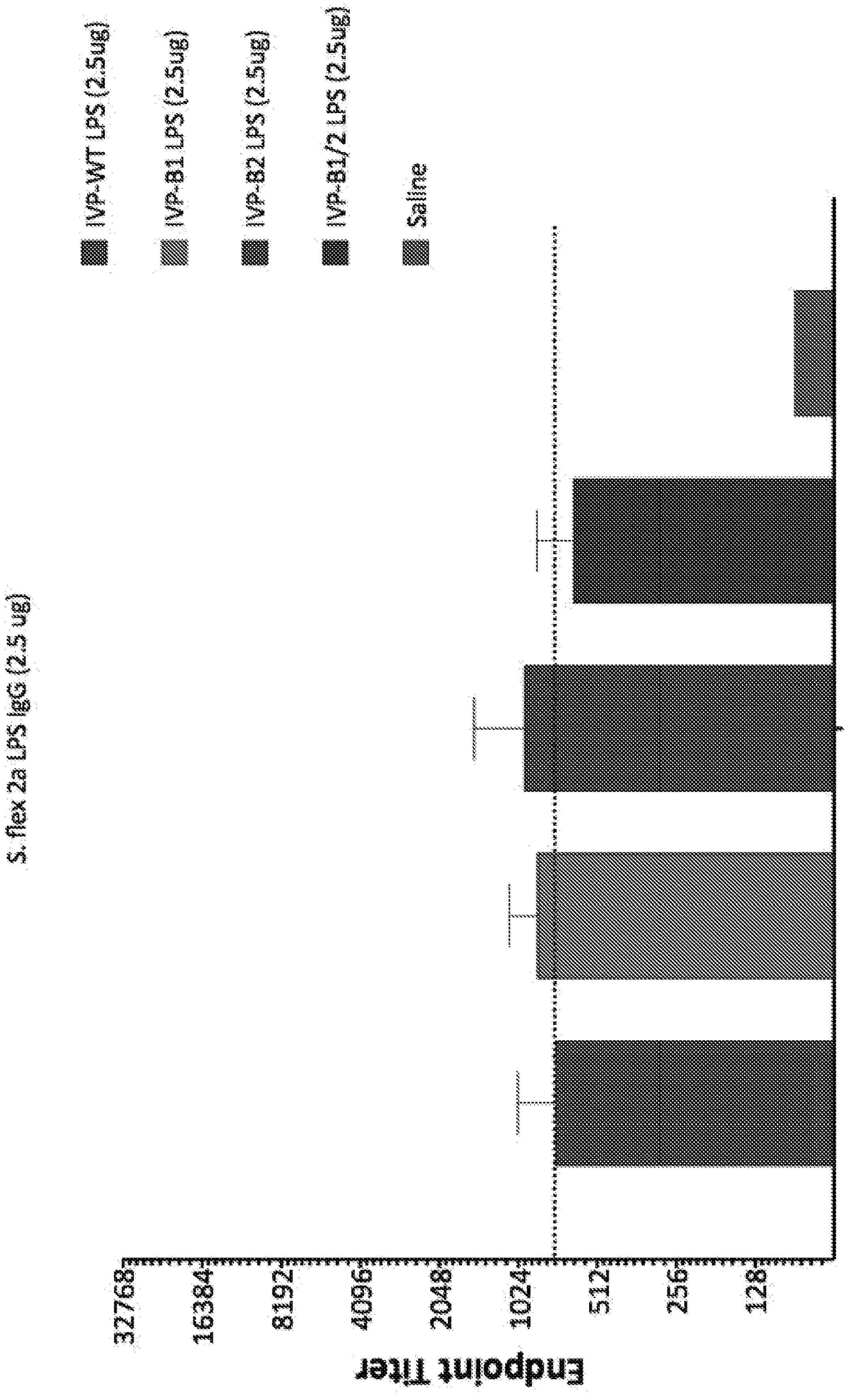
Figure 16:
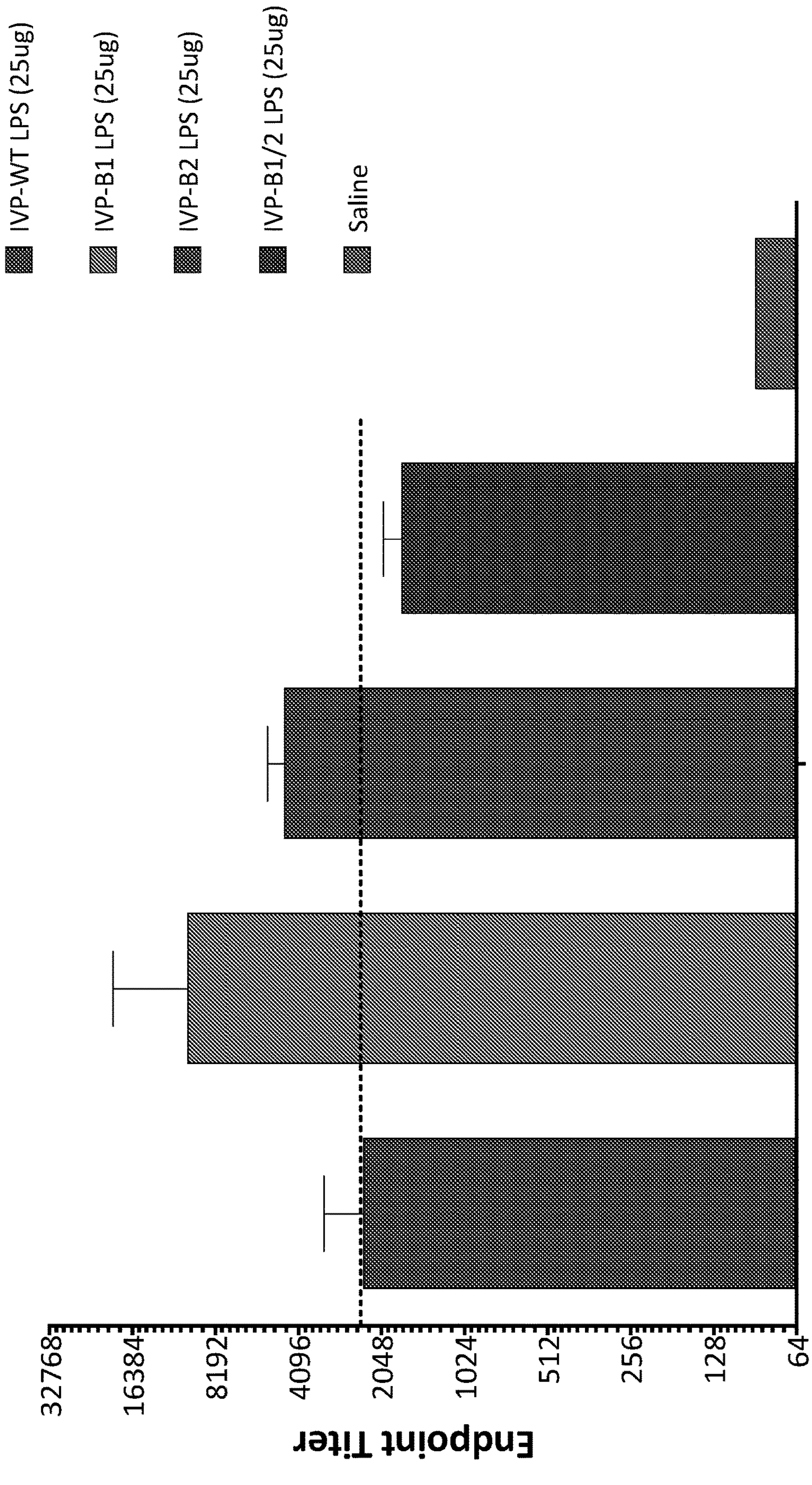

*Shigella* LPS-specific serum IgG titers (FIG. 14, FIG. 15, and FIG. 16) were comparable across all groups immunized with comparable doses of the Invaplex$_{AR}$ preparations indicating the level of acylation of LPS did not significantly influence the anti-LPS response.

Figure 17:
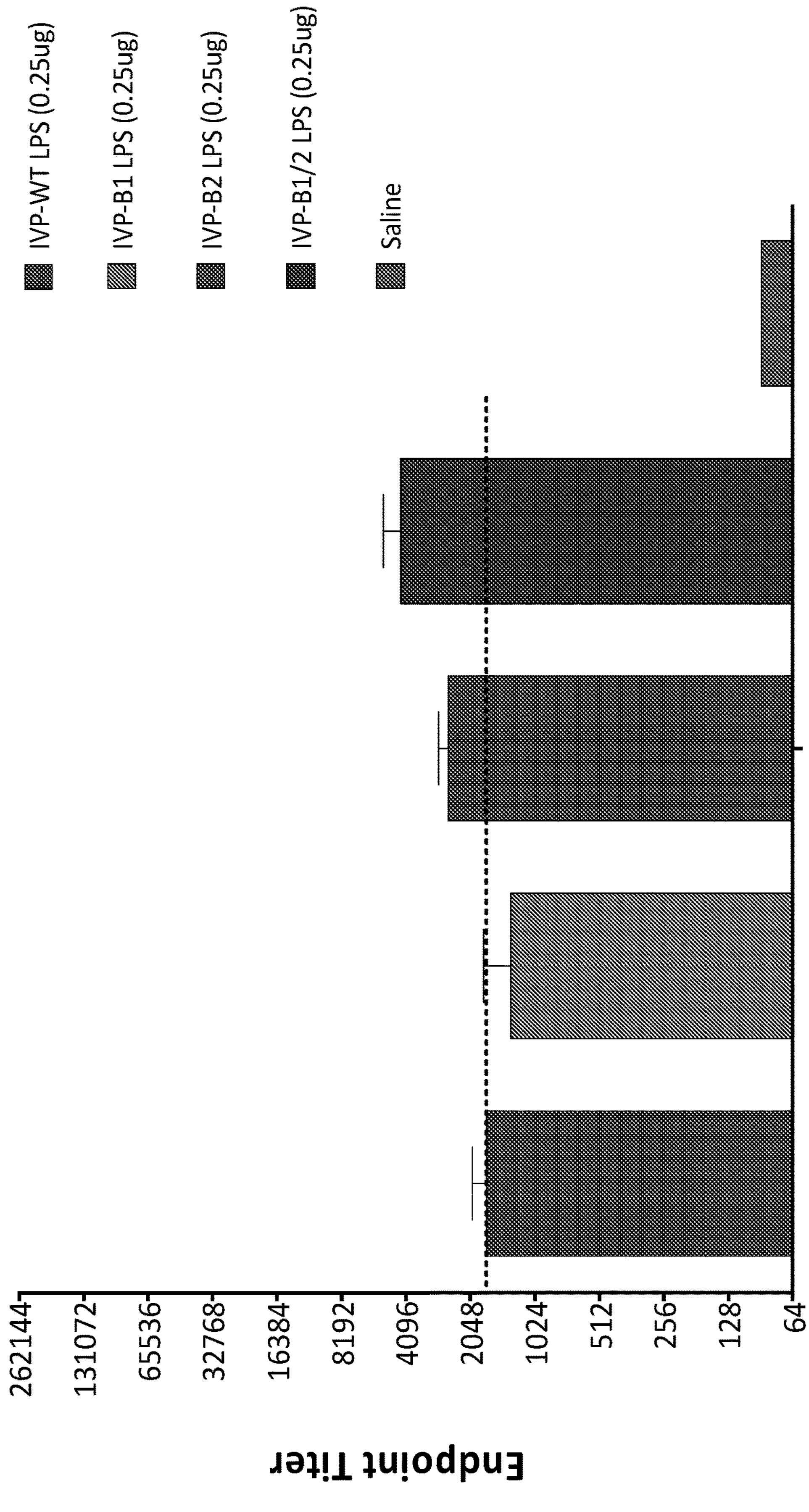
FIG. 17, FIG. 18, and FIG. 19 are graphs showing the *Shigella* Invaplex-specific serum IgG endpoint titers on day 35 from mice intradermally immunized with 0.25 μg, 2.5 μg, and 25 μg, respectively, of the indicated Invaplex$_{AR}$ preparation. As shown, the LPS of the Invaplex$_{AR}$ preparations from left to right are: WT-LPS, B1-LPS (from WR10), B2-LPS (from WR20), and B1/2-LPS (from WR30), and the last bar is saline. Dotted lines represent GMT after immunization with Invaplex$_{AR\text{-}WT}$.
Figure 18:
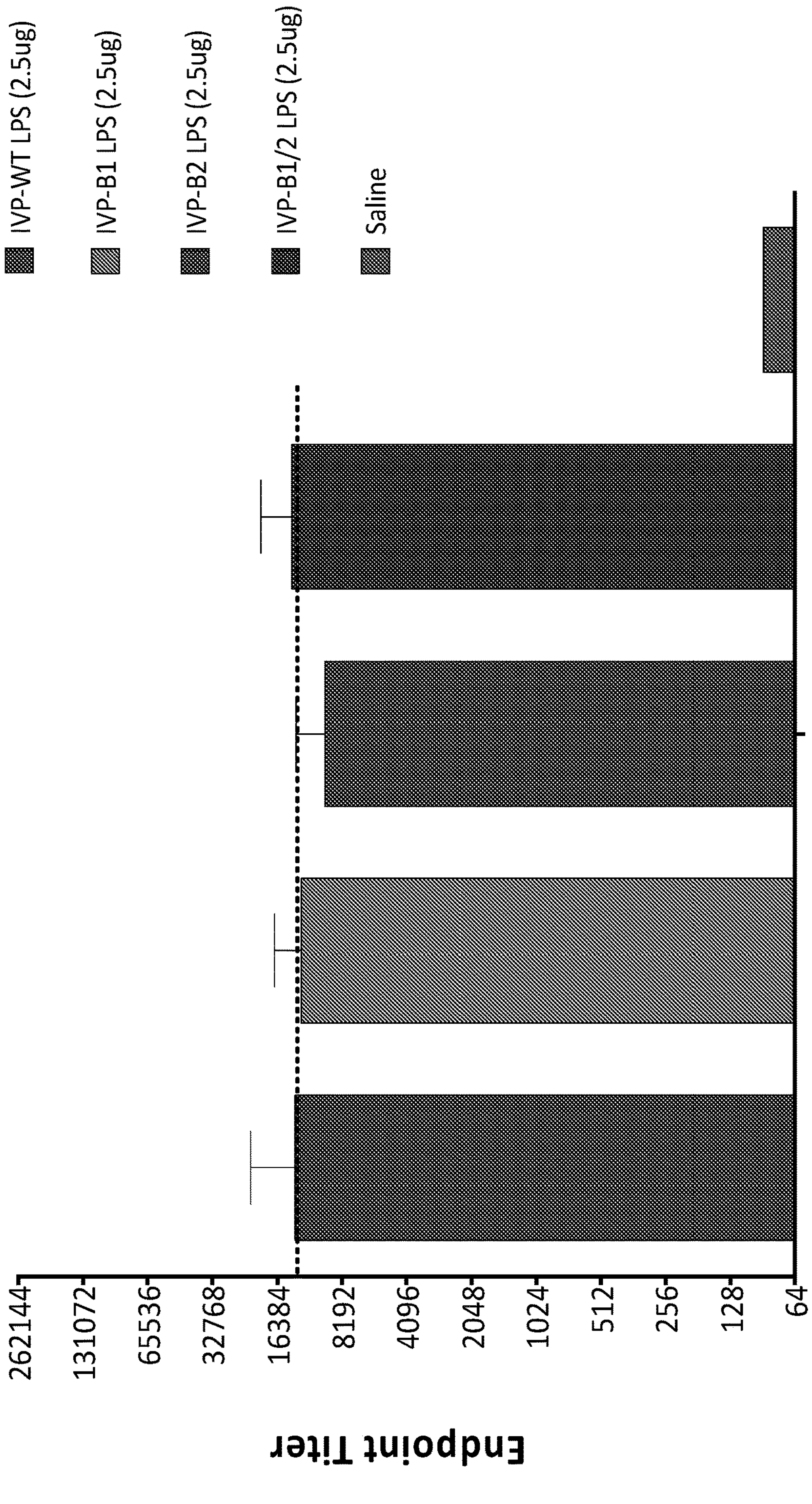
Figure 19:
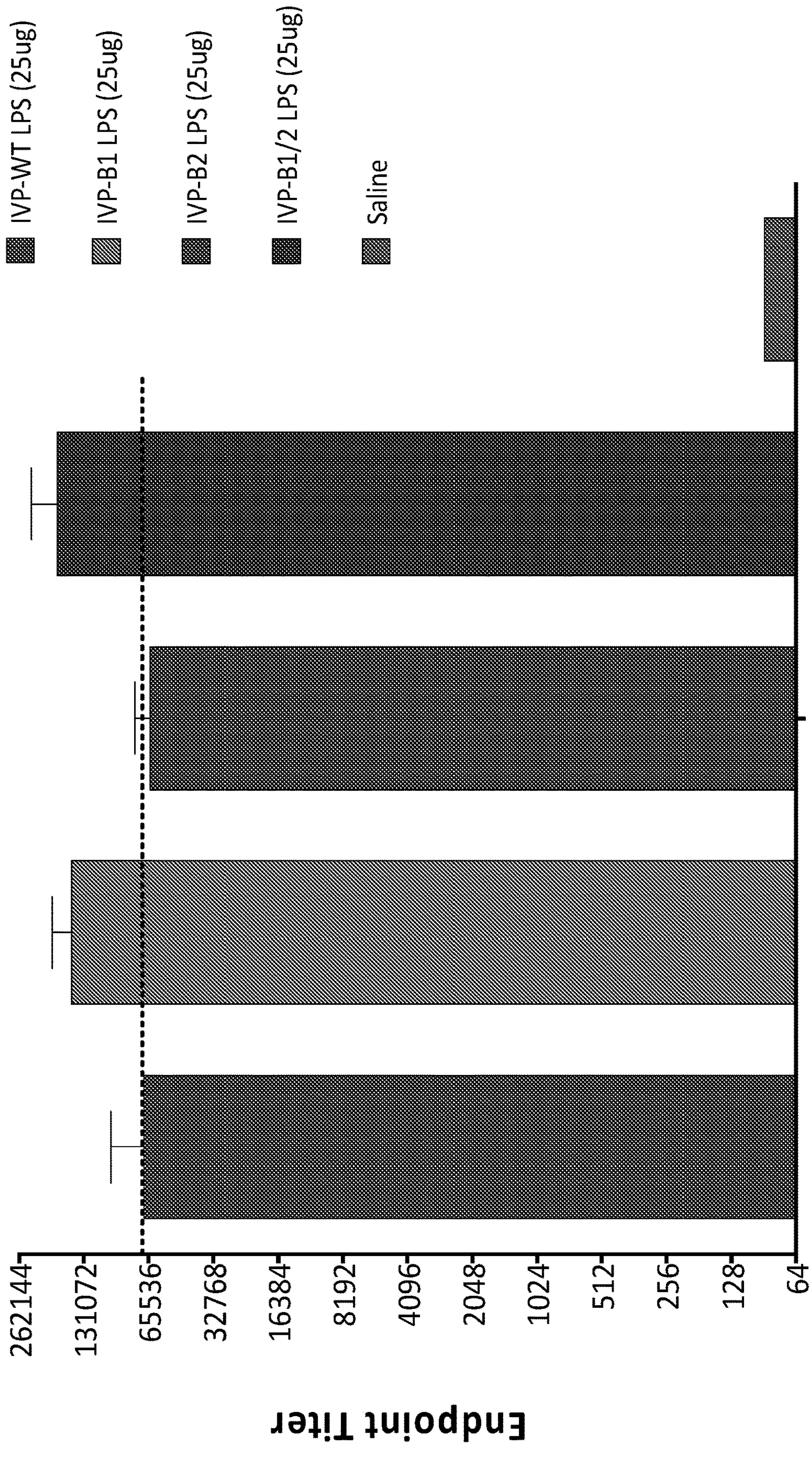

*Shigella* Invaplex 24-specific serum IgG responses (FIG. 17, FIG. 18, and FIG. 19) followed a similar trend as described above for the anti-LPS serum IgG responses in that titers were similar across all groups immunized with comparable doses of the Invaplex$_{AR}$ preparations, reinforcing the observation that LPS acylation did not significantly influence the antigen-specific response.

The serum IgA responses directed to LPS and Invaplex-24 after immunization with the Invaplex$_{AR}$ preparations (FIG. 20) were low across all groups with anti-LPS GMT ≤600 and anti-Invaplex GMTs ≤720. The LPS and Invaplex titers show dose dependency with groups immunized with 25 μg having the highest titers and responder rates. In summary, immunization with Invaplex$_{AR-Detox}$ containing LPS isolated from ΔmsbB mutant *Shigella* strains elicited comparable levels of LPS-specific and Invaplex-specific serum IgG and IgA endpoint titers to immunization with Invaplex$_{AR-WT}$. These results suggest that acylation of LPS does not significantly affect the anti-LPS serum antibody response when delivered in the context of Invaplex$_{AR}$.

Serum IgG and IgA endpoint titers directed to IpaB and IpaC (FIG. 20) largely followed a dose-dependent curve, with higher doses inducing higher antigen-specific titers.

The dose-dependent trend was more evident with IgA titers as compared to IgG titers. Interestingly, the IpaB and IpaC-specific serum IgA titers were significantly lower in groups that were immunized with Invaplex$_{AR\text{-}Detox}$ assembled with LPS isolated from msbB mutant *Shigella* strains as compared to Invaplex$_{AR\text{-}WT}$. A similar trend was seen in anti-IpaC serum IgG titers, albeit to a lesser extent. As these data suggest that the deacylated LPS may be less capable of enhancing the protein-specific antibody response as compared to Invaplex$_{AR\text{-}WT}$, additional studies in guinea pigs were conducted to further elucidate the effect of deacylated LPS on the protein-specific response and the results are provided below.

Figure 21:
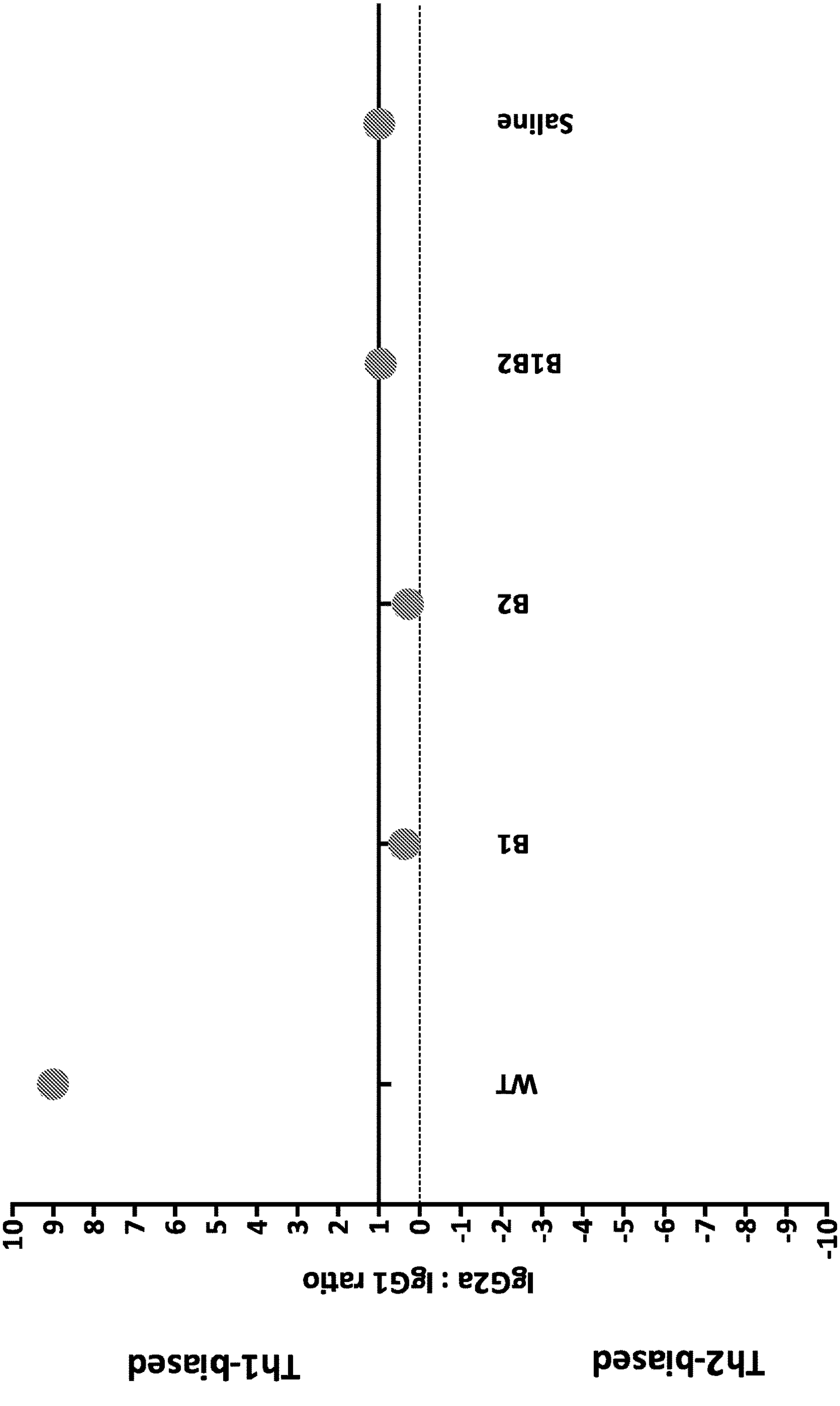
FIG. 21 is a graph showing the anti-IpaB serum IgG1 and IgG2a responses in mice immunized intradermally with 0.25 μg of Invaplex$_{AR}$ assembled with LPS isolated from wild-type *S. flexneri* 2a, 2457T or ΔmsbB1, ΔmsbB2, or ΔmsbB1/2 mutant *S. flexneri* 2a strains. WT=Invaplex$_{AR\text{-}WT}$, B1=Invaplex$_{AR\text{-}Detox}$ with LPS from WR10, B2=Invaplex$_{AR\text{-}Detox}$ with LPS from WR20, and B1B2=Invaplex$_{AR\text{-}Detox}$ with LPS from WR30.

The IpaB and IpaC serum responses suggested that the deacylated LPS contained within the Invaplex$_{AR\text{-}Detox}$ preparations may affect the overall magnitude of the immune response. The phenotype of the immune response directed towards the IpaB protein was also investigated by determining serum IgG1 and IgG2a titers and calculating the IgG2a:IgG1 ratio. Groups immunized with Invaplex$_{AR\text{-}WT}$ induced a Th1-biased immune response (FIG. 21). Interestingly, groups immunized with any one of the three Invaplex$_{AR\text{-}Detox}$ preparations containing deacylated LPS had a more balanced Th1/Th2 immune response. These data suggest that the acylation state of the lipid A may contribute to the phenotype of the immune response. The immune response phenotype may be important when creating a vaccine designed to protect against invasive enteric bacterial pathogens, such as *Shigella* spp. For example, a Th2-dominant response will provide high levels of mucosal IgA potentially capable of neutralizing the bacteria's ability to transcytose from the intestinal lumen to the basolateral surface of the colonic epithelium where infection likely occurs. At the same time, Th1-dominated responses are capable of providing help to cell-mediated immunity to limit and clear intracellular pathogens. A balanced Th1/Th2 response could potentially offer two immunological opportunities to protect against shigellosis.

Mucosal samples (intestinal and lung washes) were collected on day 35 (one week after the second and final immunization) and assayed by ELISA for antigen-specific IgA and IgG titers. *Shigella* antigen-specific intestinal IgA responses were low across all groups with all GMTs ≤35 (data not shown). Lung IgA responses were similarly low with all GMTS ≤10. *Shigella* antigen-specific lung IgG responses after immunization with the Invaplex preparations (FIG. 22) were higher than the mucosal IgA responses with 100% seroconversion in all the 25 μg groups.

Conclusions from Mouse Studies

Evaluation of reactogenicity after intradermal immunization with Invaplex$_{AR}$ assembled using WT-LPS or deacylated LPS isolated from msbB mutant *Shigella* strains suggested that deacylated LPS from the msbB double mutant had reduced erythema and edema in the mouse model. There was no significant difference in percent weight change after immunization among the different groups in each dose category.

Intradermal immunization with Invaplex$_{AR}$ assembled using WT-LPS or deacylated LPS isolated from msbB mutant *Shigella* strains resulted in comparable levels of LPS and Invaplex-specific immune responses. Immune responses generated to IpaB and IpaC were generally of comparable magnitude but there were several examples that suggested the Ipa-specific serum IgA may be impacted by the deacylated LPS. However, formulation optimizations may overcome these observations. In addition to the influence on the magnitude of the Ipa-specific responses, the immunophenotype was also different in groups immunized with Invaplex$_{AR\text{-}Detox}$ preparations as compared to Invaplex$_{AR\text{-}WT}$, with a shift from a Th1-biased response to a balanced Th1/Th2 response.

In Vivo Immunogenicity and Efficacy of Invaplex$_{AR\text{-}Detox}$ Preparations in Guinea Pigs The in vivo immunogenicity and efficacy of Invaplex$_{AR\text{-}WT}$ and Invaplex$_{AR\text{-}Detox}$ with LPS extracted from the ΔmsbB1/2 mutant strain of *S. flexneri* 2a was examined by using the guinea pig rectocolitis model. This model measures intestinal disease in the large intestine and is thought to be very similar to shigellosis in humans. Groups of male Hartley guinea pigs (5 guinea pigs/group) were immunized intranasally on days 0, 14, and 28 with dose amounts of 25 μg or 100 μg of each Invaplex$_{AR}$ preparation as outlined in Table 5 as follows:

TABLE 5

| Group | n | Vaccine | Dose (μg) |
|---|---|---|---|
| 1 | 5 | Invaplex$_{AR\text{-}WT}$ (WT-LPS) | 25 |
| 3 | 5 | Invaplex$_{AR\text{-}WT}$ (WT-LPS) | 100 |
| 5 | 5 | Invaplex$_{AR\text{-}Detox}$ (ΔmsbB1/2 LPS) | 25 |
| 7 | 5 | Invaplex$_{AR\text{-}Detox}$ (ΔmsbB1/2 LPS) | 100 |
| 9 | 5 | Saline | — |

The control group received 0.9% sterile saline (negative control). On study day 0 and 42 ocular wash samples were collected. Blood samples were collected on study days 0, 28, 42, and 58 and fecal samples were collected on study days 0 and 35. Blood, fecal, and ocular washes were assayed by ELISA for antigen-specific antibody endpoint titers. The efficacy of the Invaplex$_{AR}$ preparations was assessed on day 56 when animals were challenged intrarectally with *S. flexneri* 2a 2457T.

Guinea pigs were challenged on day 56 (4 weeks after the third immunization) with $3.5\times10^{10}$ cfu of virulent *S. flexneri* 2a 2457T. Guinea pigs were monitored daily for 48 hours post-infection. A composite disease score was calculated for each animal by adding the fecal, mucous, inflammation, and blood scores. Animals with disease scores of 8 or less were considered protected from challenge.

As summarized in FIG. 23, animals immunized with saline (negative control) were not protected against rectal challenge with mean disease scores of 10.5. Animals immunized with Invaplex$_{AR\text{-}WT}$ or Invaplex$_{AR\text{-}Detox}$ (25 μg) were not significantly protected. However, animals immunized with 100 μg Invaplex$_{AR\text{-}WT}$ or Invaplex$_{AR\text{-}Detox}$ were significantly protected (p≤0.02). These results demonstrate that intranasal immunization with Invaplex$_{AR\text{-}Detox}$ induces an immune response that is protective against intrarectal challenge with wild-type *Shigella* spp. with an efficacy substantially similar to that of Invaplex$_{AR\text{-}WT}$.

Blood collected on day 0 and 42 was analyzed by ELISA for serum IgG and IgA endpoint titers directed to *S. flexneri* 2a LPS, *S. flexneri* 2a native Invaplex 24, IpaB, and IpaC. Antigen-specific serum IgG and IgA were undetectable in samples collected before immunization (Day 0) from all guinea pigs in each treatment group. Similarly, guinea pigs immunized with saline (group 9) did not have detectable responses (titer <180).

As shown in FIG. 24, *Shigella* LPS-specific IgG titers were similar across all groups immunized with comparable doses of the various Invaplex$_{AR}$ preparations indicating that the acylation of LPS did not influence the anti-LPS response. Serum IgA responses directed to LPS were below detection (<90) in most groups. These results suggest that acylation of LPS does not affect the anti-LPS serum antibody response when delivered in the context of $Invaplex_{AR}$.

As shown in FIG. 25, *S. flexneri* 2a native Invaplex 24-specific serum IgA and IgG responses followed a similar trend as described above for the anti-LPS serum IgA and IgG responses in that titers were similar across all groups immunized with comparable doses of the $Invaplex_{AR}$ preparations. In summary, immunization with $Invaplex_{AR\text{-}Detox}$ containing LPS isolated from the ΔmsbB1/2 mutant strain elicited comparable levels of LPS and Invaplex-specific serum IgG and IgA endpoint titers as did immunization with $Invaplex_{AR\text{-}WT}$. These results suggest that acylation of LPS does not significantly affect the anti-LPS serum antibody response when delivered in the context of $Invaplex_{AR}$. Serum IgG and IgA endpoint titers directed to IpaB and IpaC were also comparable across all doses. These data suggest that deacylated LPS does not alter the anti-IpaB or IpaC serum antibody response.

Antigen-specific mucosal IgA responses were undetectable in mucosal samples collected before immunization (day 0) from all guinea pigs in each treatment group. Similarly, guinea pigs immunized with saline (group 9) did not have detectable *Shigella*-specific mucosal antibodies.

Eye-wash samples collected on day 0 and 42 were analyzed by ELISA for ocular IgA endpoint titers directed to *S. flexneri* 2a LPS, *S. flexneri* 2a native Invaplex 24, IpaB, and IpaC. Generally, guinea pigs immunized with $Invaplex_{AR\text{-}Detox}$ containing LPS isolated from the ΔmsbB1/2 mutant strain elicited similar levels of antigen-specific endpoint titers as compared to guinea pigs immunized with $Invaplex_{AR\text{-}WT}$. As shown in FIG. 26, there was no dose dependent trend in antigen-specific titers. This suggests that acylation of LPS does not affect antigen-specific mucosal responses when delivered in the context of $Invaplex_{AR}$.

Fecal samples collected on day 0 and 35 were analyzed by ELISA for fecal IgA endpoint titers directed to *S. flexneri* 2a LPS and *S. flexneri* 2a native Invaplex 24. As shown in FIG. 27, anti-LPS and anti-Invaplex 24 titers were low across all groups (GMTs ≤20).

In another series of experiments, groups of male Hartley guinea pigs (6-12 guinea pigs/group) were immunized on study days 0, 14, and 28 either intranasally, intramuscularly, or intradermally (100 μl total volume) with varying doses of $Invaplex_{AR\text{-}Detox}$ with LPS extracted from the WR30 strain of *S. flexneri* 2a as outlined in Table 6.

TABLE 6

| Group | N | Vaccine (Dose μg) | Route of Immunization |
|---|---|---|---|
| 1 | 6 | $Invaplex_{AR\text{-}Detox}$ (25 μg) | Intranasal |
| 2 | 6 | $Invaplex_{AR\text{-}Detox}$ (25 μg) | Intramuscular |
| 3 | 6 | $Invaplex_{AR\text{-}Detox}$ (5 μg) | Intramuscular |
| 4 | 6 | $Invaplex_{AR\text{-}Detox}$ (25 μg) | Intradermal |
| 5 | 6 | $Invaplex_{AR\text{-}Detox}$ (5 μg) | Intradermal |
| 6 | 12 | Saline | Intranasal |

The control group received 0.9% sterile saline (negative control). Guinea pigs were bled on study days 0, 28, 42, and 14 days after challenge (Day 63). Prior to immunization and bleeding, guinea pigs were anesthetized with a mixture of ketamine and xylazine. Blood was assayed by ELISA for antigen-specific antibody endpoint titers. The guinea pig keratoconjunctivitis model (Sereny test) was used for efficacy testing. Three weeks after the third intranasal, intradermal, or intramuscular immunization (Day 49) guinea pigs were challenged intraocularly with *S. flexneri* 2a strain 2457T (about $2.0\times10^8$ cfu per eye) and observed daily for 5 days for the occurrence of keratoconjunctivitis. Animals in the negative control group were also challenged using identical procedures. The degree of inflammation and keratoconjunctivitis was scored using a scale of 0 to 3. Eyes with no inflammation (score of 0) or slight inflammation (score of 1) at Day 5 were considered protected. Eyes with scores of 2 (keratoconjunctivitis with no purulence) or 3 (fully developed keratoconjunctivitis with purulence) were considered not protected. Efficacy was calculated by the formula: [{% disease (controls)−% disease (vaccines)}/% disease (controls)]×100.

As summarized in FIG. 28, guinea pigs immunized with saline (negative control) were not protected against keratoconjunctivitis with 100% disease in the controls. Guinea pigs immunized with 5 μg of $Invaplex_{AR\text{-}Detox}$ intramuscularly were not significantly protected on Day 5 post challenge. However, guinea pigs immunized intradermally with 5 μg of $Invaplex_{AR\text{-}Detox}$ were significantly protected on Day 5 (p=0.0373). All animals immunized with 25 μg of $Invaplex_{AR\text{-}Detox}$ either intranasally, intramuscularly, or intradermally were significantly protected on Day 5 post challenge with a protective efficacy of ≥75%. These results demonstrate that parenteral immunization with $Invaplex_{AR\text{-}Detox}$ can induce an immune response that is as protective against ocular challenge with *S. flexneri* 2a strain 2457T as compared to immunization via a mucosal route.

Conclusions from Guinea Pig Studies

Intranasal immunization with $Invaplex_{AR}$ preparations assembled using WT-LPS or LPS isolated from the ΔmsbB1/2 mutant *Shigella* strain resulted in comparable levels of LPS, native Invaplex, IpaB, and IpaC-specific immune responses. Minimal levels of mucosal antibodies were detected in fecal and ocular washes.

Animals immunized with 100 μg $Invaplex_{AR\text{-}WT}$ or $Invaplex_{AR\text{-}Detox}$ were significantly protected ($p\leq0.02$) whereas animals immunized with the lower dose (25 μg) of $Invaplex_{AR\text{-}WT}$ or $Invaplex_{AR\text{-}Detox}$ were not significantly protected. These results demonstrate that intranasal immunization with $Invaplex_{AR\text{-}Detox}$ or $Invaplex_{AR\text{-}WT}$ can induce immune responses that are protective against intrarectal challenge with virulent *S. flexneri* 2a 2457T. Therefore, in some embodiments, the present invention provides a method of immunizing a subject against one or more *Shigella* spp., which comprises administering to the subject an immunogenic amount of a $Invaplex_{AR\text{-}Detox}$ mucosally. Furthermore, parenteral immunization (e.g., intramuscular or intradermal) induced protection against ocular challenge with *S. flexneri* 2a, 2457T. Therefore, in some embodiments, the present invention provides a method of immunizing a subject against a mucosal challenge with one or more *Shigella* spp. which comprises administering to the subject an immunogenic amount of a $Invaplex_{AR\text{-}Detox}$ parenterally.

All scientific and technical terms used in this application have meanings commonly used in the art unless otherwise specified.

As used herein, the terms "subject", "patient", and "individual" are used interchangeably to refer to humans and non-human animals. The term "non-human animal" includes all vertebrates, e.g., mammals and non-mammals, such as non-human primates, horses, sheep, dogs, cows, pigs, chickens, and other veterinary subjects and test animals. In some embodiments of the present invention, the subject is a mammal. In some embodiments of the present invention, the subject is a human.

The use of the singular can include the plural unless specifically stated otherwise. As used in the specification and the appended claims, the singular forms "a", "an", and "the" can include plural referents unless the context clearly dictates otherwise. As used herein, "and/or" means "and" or "or". For example, "A and/or B" means "A, B, or both A and B" and "A, B, C, and/or D" means "A, B, C, D, or a combination thereof" and said "combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

The phrase "comprises or consists of" is used as a tool to avoid excess page and translation fees and means that in some embodiments the given thing at issue comprises something, and in some embodiments the given thing at issue consists of something. For example, the sentence "In some embodiments, the composition comprises or consists of A" is to be interpreted as if written as the following two separate sentences: "In some embodiments, the composition comprises A. In some embodiments, the composition consists of A." Similarly, a sentence reciting a string of alternates is to be interpreted as if a string of sentences were provided such that each given alternate was provided in a sentence by itself. For example, the sentence "In some embodiments, the composition comprises A, B, or C" is to be interpreted as if written as the following three separate sentences: "In some embodiments, the composition comprises A. In some embodiments, the composition comprises B. In some embodiments, the composition comprises C."

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. An artificial Invaplex comprising one or more invasin proteins complexed with a deacylated lipopolysaccharide from a gram-negative bacterial strain which is a strain of a *Shigella* spp.

2. The artificial Invaplex of claim 1, wherein the deacylated lipopolysaccharide lacks one or more fatty acid chains as compared to the corresponding wild-type lipopolysaccharide.

3. The artificial Invaplex of claim 1, wherein the deacylated lipopolysaccharide lacks one fatty acid chain as compared to the corresponding wild-type lipopolysaccharide.

4. The artificial Invaplex of claim 1, wherein the deacylated lipopolysaccharide lacks two fatty acid chains as compared to the corresponding wild-type lipopolysaccharide.

5. The artificial Invaplex of claim 1, wherein the deacylated lipopolysaccharide lacks more than two fatty acid chains as compared to the corresponding wild-type lipopolysaccharide.

6. The artificial Invaplex of claim 1, wherein the gram-negative bacterial strain is an msbB mutant strain, such as a ΔmsbB1 mutant strain, a ΔmsbB2 mutant strain, or a ΔmsbB1/ΔmsbB2 mutant strain.

7. The artificial Invaplex of claim 1, wherein the gram-negative bacterial strain is WR10, WR20, or WR30.

8. The artificial Invaplex of claim 1, wherein the one or more invasin proteins are IpaB and IpaC from *Shigella* spp.

9. The artificial Invaplex of claim 1, wherein the deacylated lipopolysaccharide was deacylated by enzymatic treatment or was obtained from a strain of a *Shigella* spp. that lacks one or more genes responsible for lipopolysaccharide acylation or has a loss-of-function mutation in one or more genes responsible for lipopolysaccharide acylation.

10. A composition comprising the artificial Invaplex of claim 1 and a pharmaceutically acceptable carrier.

11. The composition of claim 10, further comprising an immunogen.

12. The composition of claim 11, wherein the artificial Invaplex is an adjuvant for the immunogen.

13. The composition of claim 10, wherein the artificial Invaplex is present in an immunogenic amount.

14. A method for inducing an immune response in a subject, which comprises administering to the subject an immunogenic amount of the artificial Invaplex according to claim 1 or a composition thereof.

15. The method according to claim 14, wherein the immunogenic amount is administered by mucosal administration.

16. The method according to claim 14, wherein the immune response is a protective immune response.

17. The method according to claim 14, wherein the immune response is a balanced Th1/Th2 response as compared to that provided by a corresponding Invaplex comprising the corresponding wild-type lipopolysaccharide instead of the deacylated lipopolysaccharide.

18. The method or use according to claim 17, wherein the balanced Th1/Th2 response is a protective immune response.

* * * * *